United States Patent
Fuh et al.

(10) Patent No.: US 12,006,360 B2
(45) Date of Patent: Jun. 11, 2024

(54) DUAL SPECIFIC ANTIBODIES FOR BINDING INTERLEUKIN 4 (IL4) AND INTERLEUKIN 5 (IL5)

(71) Applicant: Genentech, Inc., South San Francisco, CA (US)

(72) Inventors: Germaine Fuh, Pacifica, CA (US); Chingwei V. Lee, Foster City, CA (US); Patrick Koenig, San Francisco, CA (US)

(73) Assignee: Genentech, Inc., South San Francisco, CA (US)

( * ) Notice: Subject to any disclaimer, the term of this patent is extended or adjusted under 35 U.S.C. 154(b) by 675 days.

(21) Appl. No.: 16/860,891

(22) Filed: Apr. 28, 2020

(65) Prior Publication Data

US 2020/0255512 A1    Aug. 13, 2020

Related U.S. Application Data

(60) Division of application No. 15/167,030, filed on May 27, 2016, now Pat. No. 10,683,348, which is a continuation of application No. PCT/US2014/071193, filed on Dec. 18, 2014.

(60) Provisional application No. 61/946,547, filed on Feb. 28, 2014, provisional application No. 61/919,552, filed on Dec. 20, 2013.

(51) Int. Cl.
| | |
|---|---|
| A61K 39/395 | (2006.01) |
| A61K 45/06 | (2006.01) |
| C07K 16/24 | (2006.01) |
| C07K 16/46 | (2006.01) |
| A61K 39/00 | (2006.01) |

(52) U.S. Cl.
CPC ........ *C07K 16/244* (2013.01); *A61K 39/3955* (2013.01); *A61K 45/06* (2013.01); *C07K 16/247* (2013.01); *C07K 16/468* (2013.01); *A61K 2039/505* (2013.01); *C07K 2317/14* (2013.01); *C07K 2317/21* (2013.01); *C07K 2317/31* (2013.01); *C07K 2317/56* (2013.01); *C07K 2317/565* (2013.01); *C07K 2317/567* (2013.01); *C07K 2317/92* (2013.01)

(58) Field of Classification Search
None
See application file for complete search history.

(56) References Cited

U.S. PATENT DOCUMENTS

| | | |
|---|---|---|
| 10,118,970 B2 | 11/2018 | Fuh et al. |
| 2008/0069820 A1 | 3/2008 | Fuh et al. |
| 2014/0206846 A1 | 7/2014 | Beckmann |

FOREIGN PATENT DOCUMENTS

| | | |
|---|---|---|
| BR | 112015024553 A2 | 10/2017 |
| EP | 2050764 A1 | 4/2009 |
| WO | WO-02/02773 A2 | 1/2002 |
| WO | WO-03/002609 A2 | 1/2003 |
| WO | WO-2010/108127 A1 | 9/2010 |
| WO | WO-2010/136483 A2 | 12/2010 |
| WO | WO-2012163520 A1 | 12/2012 |
| WO | WO-2014/165771 A2 | 10/2014 |

OTHER PUBLICATIONS

Paul, Fundamental Immunology, 3rd Edition, 1993, pp. 292-295, under the heading "Fv Structure and Diversity in Three Dimensions".*
Rudikoff et al. (PNAS 79: 1979-1983, 1982).*
MacCallum et al. (J. Mol. Biol. 262: 732-745, 1996).*
De Pascalis et al. (J. Immunol. 169: 3076-3084, 2002).*
Casset et al. (Biochem. Biophys. Res. Comm. 307: 198-205, 2003).*
Chen et al. (J. Mol. Biol. 293: 865-881, 1999).*
Wu et al. (J. Mol. Biol. 294: 151-162, 1999).*
"CDR-H3 diversity is not required for antigen recognition by synthetic antibodies," available in PMC Feb. 22, 2014, published in final edited form as: J Mol Biol. 425(4):803-11 (2013) (15 pages).
"Structure of a clade C HIV-1 gp120 bound to CD4 and CD4-induced antibody reveals anti-CD4 polyreactivity," available in PMC Nov. 1, 2010, published in final edited form as: Nat Struct Mol Biol. 17(5):608-13 (2010) (16 pages).
Almaro et al., "Humanization of antibodies," Front Biosci. 13:1619-33 (2008).
Barthelemy et al., "Comprehensive analysis of the factors contributing to the stability and solubility of autonomous human VH domains," J Biol Chem. 283(6):3639-54 (2008) (17 pages).
Beiboer et al., "Guided selection of a pan carcinoma specific antibody reveals similar binding characteristics yet structural divergence between the original murine antibody and its human equivalent," J Mol Biol. 296(3):833-849 (2000).

(Continued)

*Primary Examiner* — Christine J Saoud
(74) *Attorney, Agent, or Firm* — Clark & Elbing LLP; Thomas J. Takara

(57) ABSTRACT

The invention provides dual specific antibodies capable of binding interleukin 4 (IL4) and interleukin 5 (IL5) and methods of making and using such antibodies. In general, the dual specific antibodies capable of binding IL4 and IL5 are generated by identification of a monospecific antibody having light chain variable region $V_L$ residues that are electrostatic or hydrophobic and altering the nucleic acid sequence encoding one or more solvent accessible residues in the $V_H$ of the antibody either alone or in combination with alteration of the nucleic acid sequence encoding the $V_L$ of the antibody. The altered $V_H$ and the $V_L$ are expressed and dual specific antibodies, or antigen-binding fragments thereof, are selected.

11 Claims, 15 Drawing Sheets

Specification includes a Sequence Listing.

(56) References Cited

OTHER PUBLICATIONS

Choi et al., "Predicting antibody complementarity determining region structures without classification," Mol Biosyst. 7(12):3327-34 (2011).
De Genst et al., "Antibody repertoire development in camelids," Dev Comp Immunol. 30(1-2):187-98 (2006).
Diskin et al., "Structure of a clade C HIV-1 gp120 bound to CD4 and CD4-induced antibody reveals anti-CD4 polyreactivity," Nat Struct Mol Biol. 17(5):608-13 (2010). (19 pages).
Eigenbrot et al., "Two-in-One antibodies with dual action Fabs," Curr Op Chem Biol. 17(3):400-5 (2013).
Griffiths et al., "Human anti-self antibodies with high specificity from phage display libraries," EMBO J. 12(2):725-34 (1993).
Klimka et al., "Human anti-CD30 recombinant antibodies by guided phage antibody selection using cell panning," Br J Cancer. 83(2):252-60 (2000).
Knappik et al., "Fully Synthetic Human Combinatorial Antibody Libraries (HuCAL) Based on Modular Consensus Frameworks and CDRs Randomized with Trinucleotides," J Mol Biol. 296(1):57-86 (2000) (30 pages.).
Koenig et al., Chapter 11: Two-in-One Antibodies. Bispecific Antibodies. Kontermann (ed.), Springer-Verlag Berlin Heidelberg, Germany, 187-98 (2011).
Kontermann, "Dual targeting strategies with bispecific antibodies," MAbs. 4(2):182-97 (2012).
Lee et al., "A two-in-one antibody engineered from a humanized interleukin 4 antibody through mutation in heavy chain complementarity-determining regions," MABS. 6(3):622-7 (2014).
Persson et al., "CDR-H3 diversity is not required for antigen recognition by synthetic anitbodies," J Mol Biol. 425(4):803-11 (2012). (15 pages).
Ravn et al., "Deep sequencing of phage display libraries to support antibody discovery," Methods. 60(1):99-110 (2013).
Schaefer et al., "A two-in-one antibody against HER3 and EGFR has superior inhibitory activity compared with monospecific antibodies," Cancer Cell. 20(4):472-86 (2011).
Sela-Culang et al., "A systematic comparison of free and bound antibodies reveals binding-related conformational changes," J Immunol. 189(10):4890-9 (2012) (11 pages).
Spiess et al., "Development of a human IgG4 bispecific antibody for dual targeting of interleukin-4 (IL-4) and interleukin-13 (IL-13) cytokines," J Biol Chem. 288(37):26583-93 (2013).
Tsumoto et al., "Novel selection method for engineered antibodies using the mechanism of Fv fragment stabilization in the presence of antigen," Protein Eng. 10(11):1311-8 (1997).
Ward et al., "Binding activities of a repertoire of single immunoglobulin variable domains secreted from *Escherichia coli*," Nature. 341(6242):544-6 (1989).
Yasukawa et al., "IL-6 induces an anti-inflammatory response in the absence of SOCS3 in macrophages," Nat Immunol. 4(6):551-6 (2003).

\* cited by examiner

Figure 2B

HEAVY CHAIN

| Clones | \_ | CDR-H1 | \_ | \_ | \_ | \_ | \_ | \_ | \_ | CDR-H2 | \_ | \_ | \_ | \_ | \_ | \_ | \_ | \_ | \_ | \_ | \_ | \_ | CDR-H3 | \_ | \_ | \_ | \_ | \_ | \_ | \_ |
|---|---|---|---|---|---|---|---|---|---|---|---|---|---|---|---|---|---|---|---|---|---|---|---|---|---|---|---|---|---|---|
|  | 28 | 29 | 30 | 31 | 32 | 33 | 34 | 35 | 49 | 50 | 51 | 52 | 52a | 52b | 52c | 53 | 54 | 55 | 56 | 57 | 58 | 95 | 96 | 97 | 98 | 99 | 100 | 100a | 101 | 102 |
| 19C11 | T | F | T | D | Y | S | M | H | V | W | I | N | T |   |   | E | T | G | E | P | T | E | G | I | F | Y | G | M | D | Y |
| 5A |   |   |   |   |   | D | I |   | A | G |   | V | Y | Y | Y | D |   |   |   |   |   |   |   |   |   |   |   |   |   |   |
| E7 |   |   |   |   |   |   |   |   | A | V |   | V | S | D | A | A |   |   | F | T | Y |   | I |   |   |   |   |   |   |   |
| B1 |   |   |   |   |   | F | I |   | G | V |   | F | Q | - | S | I |   |   | R | T | Y |   |   |   |   |   |   |   |   |   |
| F1 |   |   |   |   |   | L | M |   | G | I |   | F | Y | S | - | - | S |   | A | T | Y |   |   | L |   |   |   |   |   |   |
| F2 |   |   |   |   |   |   |   |   |   |   |   |   |   |   |   | - |   |   | H | T | Y |   |   |   |   |   |   |   |   |   |

LIGHT CHAIN

| Clones | CDR-L1 | | | | | | | CDR-L2 | | | | | | CDR-L3 | | | | | | | |
|---|---|---|---|---|---|---|---|---|---|---|---|---|---|---|---|---|---|---|---|---|---|
|  | 28 | 29 | 30 | 31 | 32 | 33 | 34 | 50 | 51 | 52 | 53 | 54 | 55 | 89 | 91 | 92 | 93 | 94 | 95 | 95a | 96 |
| 19C11 | S | V | I | N | D | A | A | Y | T | S | H | R | Y | D | Y | T | S | P |   |   | W |
| 5A |   |   |   |   |   |   |   |   |   |   |   |   |   |   |   |   |   |   |   |   |   |
| E7 |   |   |   |   |   |   |   |   |   |   |   |   |   |   |   |   |   | P | F | P | L |
| B1 |   |   |   |   |   |   |   |   |   |   |   |   |   |   |   |   |   |   |   |   |   |
| F1 |   |   |   |   |   |   |   |   |   |   |   |   |   |   |   |   |   |   |   |   |   |
| F2 |   |   |   |   |   |   |   |   |   |   |   |   |   |   |   |   |   |   |   |   |   |

Phage IC50 (nM)

| Clones | IL4 | IL5 | IL13 |
|---|---|---|---|
| 19C11 | 1.1 | NB | NB |
| 5A | NB | ~1000 | NB |
| E7 | 0.7 | ~1000 | NB |
| B1 | ~1000 | ~1000 | NB |
| F1 | 22.3 | NB | ~1000 |
| F2 | 14.8 | NB | ~1000 |

Figure 4A

Light Chain Sequence Summary

| Kabat# | 1 | 2 | 3 | 4 | 5 | 6 | 7 | 8 | 9 | 10 | 11 | 12 | 13 | 14 | 15 | 16 | 17 | 18 | 19 | 20 | 21 | 22 | 23 | 24 | 25 | 26 | 27 | A | B | C | D | E | F | 28 | 29 | 30 | 31 | 32 | 33 | 34 | 35 | 36 | 37 |
|---|---|---|---|---|---|---|---|---|---|---|---|---|---|---|---|---|---|---|---|---|---|---|---|---|---|---|---|---|---|---|---|---|---|---|---|---|---|---|---|---|---|---|---|
| | | | | | | | | | | | | | | | | | | | | | | | | Kabat - CDR L1 | | | | | | | | | | | | | | | | | | | |
| | | | | | | | | | | | | | | | | | | | | | | | | | | | | | | | | | | | | | | | | Contact - CDR L1 | | |
| 19C11.KI | D | I | Q | M | T | Q | S | P | S | S | L | S | A | S | V | G | D | R | V | T | I | T | C | K | A | S | Q | S | V | I | N | | | D | A | A | W | Y | Q |
| 5A | | | | | | | | | | | | | | | | | | | | | | | | K | A | S | Q | S | V | I | N | | | D | A | A | | | |
| E7 | | | | | | | | | | | | | | | | | | | | | | | | K | A | S | Q | S | V | I | N | | | D | A | A | | | |
| B1 | | | | | | | | | | | | | | | | | | | | | | | | K | A | S | Q | S | V | I | N | | | D | A | A | | | |

| Kabat# | 38 | 39 | 40 | 41 | 42 | 43 | 44 | 45 | 46 | 47 | 48 | A | 49 | 50 | 51 | 52 | 53 | 54 | 55 | 56 | 57 | 58 | 59 | 60 | 61 | 62 | 63 | 64 | 65 | 66 | 67 | 68 | 69 | 70 | 71 | 72 | 73 | 74 | 75 | 76 | 77 | 78 | 79 |
|---|---|---|---|---|---|---|---|---|---|---|---|---|---|---|---|---|---|---|---|---|---|---|---|---|---|---|---|---|---|---|---|---|---|---|---|---|---|---|---|---|---|---|---|
| | | | | | | | | | | | | | | | | Kabat - CDR L2 | | | | | | | | | | | | | | | | | | | | | | | | | | | |
| | | | | | | | | | | | | | | | | | Chothia - CDR L2 | | | | | | | | | | | | | | | | | | | | | | | | | |
| | | | | | | | | | | | | | | | | | | | | Contact - CDR L2 | | | | | | | | | | | | | | | | | | | | | | |
| 19C11.KI | Q | K | P | G | K | A | P | K | L | L | I | | | Y | Y | T | S | H | R | Y | T | G | V | P | S | R | F | S | G | S | G | S | G | T | D | F | T | L | T | I | S | S | L |
| 5A | | | | | | | | | | | | | | Y | Y | T | S | H | R | Y | T | | | | | | | | | | | | | | | | | | | | | | |
| E7 | | | | | | | | | | | | | | Y | Y | T | S | H | R | Y | T | | | | | | | | | | | | | | | | | | | | | | |
| B1 | | | | | | | | | | | | | | Y | Y | T | S | H | R | Y | T | | | | | | | | | | | | | | | | | | | | | | |

| Kabat# | 81 | 82 | 83 | 84 | 85 | 86 | 87 | 88 | 89 | 90 | 91 | 92 | 93 | 94 | 95 | A | B | C | D | E | F | 96 | 97 | 98 | 99 | 100 | 101 | 102 | 103 | 104 | 105 | 106 | 107 | 108 | |
|---|---|---|---|---|---|---|---|---|---|---|---|---|---|---|---|---|---|---|---|---|---|---|---|---|---|---|---|---|---|---|---|---|---|---|---|
| | | | | | | | | | | | | | | | Kabat - CDR L3 | | | | | | | | | | | | | | | | | | | | |
| | | | | | | | | | | | | | | | Chothia - CDR L3 | | | | | | | | | | | | | | | | | | | | |
| | | | | | | | | | | | | | | | Contact - CDR L3 | | | | | | | | | | | | | | | | | | | | |
| 19C11.KI | E | D | F | A | T | Y | Y | C | Q | Q | Y | D | Y | T | S | P | | | | | | W | T | F | G | Q | G | T | K | V | E | I | K | R | SEQ ID No: 1 |
| 5A | | | | | | | | | Q | Q | Y | D | Y | T | S | P | | | | | | W | T | | | | | | | | | | | | SEQ ID No: 1 |
| E7 | | | | | | | | | Q | Q | Y | D | Y | T | S | P | | | | | | W | T | | | | | | | | | | | | SEQ ID No: 1 |
| B1 | | | | | | | | | Q | Q | Y | D | Y | T | F | P | | | | | | L | T | | | | | | | | | | | | SEQ ID No: 5 |

Figure 4B

Heavy Chain Sequence Summary

| Kabat# | 1 | 2 | 3 | 4 | 5 | 6 | 7 | 8 | 9 | 10 | 11 | 12 | 13 | 14 | 15 | 16 | 17 | 18 | 19 | 20 | 21 | 22 | 23 | 24 | 25 | 26 | 27 | 28 | 29 | 30 | 31 | 32 | 33 | 34 | 35 | A | B | 36 | 37 | 38 | 39 | 40 | 41 |
|---|---|---|---|---|---|---|---|---|---|---|---|---|---|---|---|---|---|---|---|---|---|---|---|---|---|---|---|---|---|---|---|---|---|---|---|---|---|---|---|---|---|---|---|
| 19C11.VH1 | E | V | Q | L | V | Q | S | G | A | E | V | K | K | P | G | A | S | V | K | V | S | C | K | A | S | G | Y | T | F | T | D | Y | S | M | H | | | W | V | R | Q | A | P |
| 5A | | | | | | | | | | | | | | | | | | | | | | | | | | | | | | | | | | | H | | | | | | | | |
| E7 | | | | | | | | | | | | | | | | | | | | | | | | | | | G | Y | T | F | T | D | Y | R | I | | | | | | | | |
| B1 | | | | | | | | | | | | | | | | | | | | | | | | | | | G | Y | T | F | T | D | Y | Y | M | | | | | | | | |
| | | | | | | | | | | | | | | | | | | | | | | | | | | | G | Y | T | F | T | D | Y | M | H | | | | | | | | |

Kabat - CDR H1
Chothia - CDR H1
Contact - CDR H1

| Kabat# | 42 | 43 | 44 | 45 | 46 | 47 | 48 | 49 | 50 | 51 | 52 | a | b | c | 53 | 54 | 55 | 56 | 57 | 58 | 59 | 60 | 61 | 62 | 63 | 64 | 65 | 66 | 67 | 68 | 69 | 70 | 71 | 72 | 73 | 74 | 75 | 76 | 77 | 78 | 79 | 80 |
|---|---|---|---|---|---|---|---|---|---|---|---|---|---|---|---|---|---|---|---|---|---|---|---|---|---|---|---|---|---|---|---|---|---|---|---|---|---|---|---|---|---|---|
| 19C11.VH1 | G | Q | G | L | E | W | I | V | W | I | N | T | | | E | T | G | E | P | T | Y | A | D | D | F | K | K | G | R | V | T | I | T | R | D | T | S | T | S | T | A | Y |
| 5A | | | | | | | | | W | I | N | T | | | E | T | G | E | P | T | Y | A | D | D | F | K | K | G | | | | | | | | | | | | | | |
| E7 | | | | | | | | | A | V | I | Y | | | D | A | T | G | F | T | T | Y | A | D | D | F | K | G | | | | | | | | | | | | | | |
| B1 | | | | | | | | | A | V | I | Y | | | S | L | T | G | R | T | V | V | A | D | D | F | K | G | | | | | | | | | | | | | | |

Kabat - CDR H2
Chothia - CDR H2
Contact - CDR H2

| Kabat# | 81 | 82 | A | B | C | 83 | 84 | 85 | 86 | 87 | 88 | 89 | 90 | 91 | 92 | 93 | 94 | 95 | 96 | 97 | 98 | 99 | 100 | A | B | C | D | E | F | G | H | I | J | K | 101 | 102 | 103 | 104 | 105 | 106 | 107 | 108 | 109 | 110 | 111 | 112 | 113 |
|---|---|---|---|---|---|---|---|---|---|---|---|---|---|---|---|---|---|---|---|---|---|---|---|---|---|---|---|---|---|---|---|---|---|---|---|---|---|---|---|---|---|---|---|---|---|---|---|
| 19C11.VH1 | E | L | S | S | L | R | S | E | D | T | A | V | Y | Y | C | A | R | G | G | I | F | Y | G | | | | | | | | | | | | M | D | Y | W | G | Q | G | T | L | V | T | V | S | S |
| 5A | | | | | | | | | | | | | | | | | | G | L | L | F | Y | G | | | | | | | | | | | | M | D | Y | | | | | | | | | | | |
| E7 | | | | | | | | | | | | | | | | | | G | G | I | F | Y | G | | | | | | | | | | | | M | D | Y | | | | | | | | | | | |
| B1 | | | | | | | | | | | | | | | | | | G | G | I | F | Y | G | | | | | | | | | | | | M | D | Y | | | | | | | | | | | |

Kabat - CDR H3
Chothia - CDR H3
Contact - CDR H3

SEQ ID No: 2
SEQ ID No: 3
SEQ ID No: 4
SEQ ID No: 6

Figure 4C

Heavy Chain Sequence Summary

| Kabat# | 1 | 2 | 3 | 4 | 5 | 6 | 7 | 8 | 9 | 10 | 11 | 12 | 13 | 14 | 15 | 16 | 17 | 18 | 19 | 20 | 21 | 22 | 23 | 24 | 25 | 26 | 27 | 28 | 29 | 30 | 31 | 32 | 33 | 34 | 35 | 35A | 35B | 36 | 37 | 38 | 39 | 40 | 41 |
|---|---|---|---|---|---|---|---|---|---|---|---|---|---|---|---|---|---|---|---|---|---|---|---|---|---|---|---|---|---|---|---|---|---|---|---|---|---|---|---|---|---|---|---|
| 19C11.VH1 | E | V | Q | L | V | Q | S | G | A | E | V | K | K | P | G | A | S | V | K | V | S | C | K | A | S | G | Y | T | F | T | D | Y | S | M | H | | | W | V | R | Q | A | P |
| F1 | | | | | | | | | | | | | | | | | | | | | | | | | | G | Y | T | F | T | D | Y | S | M | H | | | | | | | | |
| F2 | | | | | | | | | | | | | | | | | | | | | | | | | | G | Y | T | F | T | D | Y | S | M | H | | | | | | | | |

| Kabat# | 42 | 43 | 44 | 45 | 46 | 47 | 48 | 49 | 50 | 51 | 52 | 52a | 52b | 52c | 53 | 54 | 55 | 56 | 57 | 58 | 59 | 60 | 61 | 62 | 63 | 64 | 65 | 66 | 67 | 68 | 69 | 70 | 71 | 72 | 73 | 74 | 75 | 76 | 77 | 78 | 79 | 80 |
|---|---|---|---|---|---|---|---|---|---|---|---|---|---|---|---|---|---|---|---|---|---|---|---|---|---|---|---|---|---|---|---|---|---|---|---|---|---|---|---|---|---|---|
| 19C11.VH1 | G | Q | G | L | E | W | I | G | W | I | N | T | | | E | T | G | E | P | T | Y | A | D | D | F | K | G | R | V | T | I | T | R | D | T | S | T | S | T | A | Y | L |
| F1 | | | | | | | | | | | | | | | | | G | K | | | Y | A | Q | D | F | K | G | | | | | | | | | | | | | | | |
| F2 | | | | | | | | | | | | | | | | | T | N | | | Y | A | Q | D | F | K | G | | | | | | | | | | | | | | | |

| Kabat# | 81 | 82 | 82A | 82B | 82C | 83 | 84 | 85 | 86 | 87 | 88 | 89 | 90 | 91 | 92 | 93 | 94 | 95 | 96 | 97 | 98 | 99 | 100 | 100A | 100B | 100C | 100D | 100E | 100F | 100G | 100H | 100I | 100J | 100K | 101 | 102 | 103 | 104 | 105 | 106 | 107 | 108 | 109 | 110 | 111 | 112 | 113 | |
|---|---|---|---|---|---|---|---|---|---|---|---|---|---|---|---|---|---|---|---|---|---|---|---|---|---|---|---|---|---|---|---|---|---|---|---|---|---|---|---|---|---|---|---|---|---|---|---|---|
| 19C11.VH1 | E | L | S | S | L | R | S | E | D | T | A | V | Y | Y | C | A | R | G | G | I | F | Y | G | | | | | | | | | | | | M | D | Y | W | G | Q | G | T | L | V | T | V | S | S | SEQ ID No: 7 |
| F1 | | | | | | | | | | | | | | | | | | G | G | I | F | Y | G | | | | | | | | | | | | M | D | Y | | | | | | | | | | | SEQ ID No: 8 |
| F2 | | | | | | | | | | | | | | | | | | G | G | I | F | Y | G | | | | | | | | | | | | M | D | Y | | | | | | | | | | | |

Figure 7A

| | CDR-L3 | | | | | | | | | CDR-H2 | | | | | | | | | | | | | | | | FR3 | | | | | | | | | | | | | Phage IC50 (nM) | |
|---|---|---|---|---|---|---|---|---|---|---|---|---|---|---|---|---|---|---|---|---|---|---|---|---|---|---|---|---|---|---|---|---|---|---|---|---|---|---|---|---|
| | 89 | 90 | 91 | 92 | 93 | 94 | 95 | 95a | 96 | 97 | 49 | 50 | 51 | 52 | a | b | 53 | 54 | 55 | 56 | 57 | 58 | 59 | 60 | 61 | 62 | 63 | 64 | 65 | 66 | 67 | 68 | 69 | 70 | 71 | 72 | 73 | 74 | 75 | 76 | 77 | 78 | IL5 | IL4 |
| Clone | Q | Q | D | Y | T | S | P | W | T | F | A | G | I | V | Y | D | A | T | G | F | T | T | Y | A | D | D | F | K | G | R | X | T | I | T | R | D | T | S | T | S | T | X | | |
| E7 | | | | | | | | | | | | | | | | | | | | | | | | | | | | | | | | | | | | | | | | | | | ~1000 | 0.7 |
| 1C.3 | | | | | | | | | | | | G | | | | | | | | | | | | | V | E | | | | | | | | | | | | | | | | | ~1000 | 4.2 |
| 1C.11 | | | | I | | | | H | | | | G | | | | | | | I | | | | | | | E | N | | | | | | | | | | | | | | | | ~1000 | 4.1 |
| 1C.24 | | | | L | | | | H | | | | G | | | | | | | | | | | | | | E | S | | | | | | | | | | | | | | | | ~1000 | 3.1 |
| 1C.27 | | | | | | | | H | | | | G | | | | | | | I | | | | | | | | | | | | | | | | | | | | | | | | 18.2 | 0.7 |
| 1C.36 | | | | | | | | H | | | | G | | | | | | | | | | | | | E | E | | | | | | | | | | | | | | | | | 0.9 | 2.1 |
| 1C.42 | | | | | | | | H | | | | G | | | | | | | | | | | | | E | S | | | | | | | | | | | | | | | | | 8.5 | 0.6 |
| 1C.59 | | | | | | | | | | | | | | | | | | | | | | | | | | I | | | | | | | | | | | | | | | | | n/a | n/a |
| 1C.60 | | | | | | | K | | | | | | | | | | | | V | | | | | | E | | | | | | | | | | | | | | | | | | 3.67 | 1.1 |
| 1C.91 | | | | | | | | | | | | G | | | | | | | V | | | | | | | | | | | | | | | | | | | | | | | | ~1000 | 4 |
| 1C.93 | | | | | | | | H | | | | G | | | | | | | A | | | | | | | | | | | | | | | | | | | | | | | | ~1000 | n/a |
| 1C.94 | | | | | | | | | | | | G | | | | | | | | | | | | | | | | | | | | | | | | | | | | | | | ~1000 | n/a |
| 2B.6 | | | | | | | | | | | | | | | | | | | | | | | | | L | | | | | | | I | | | | | | | | | | | ~1000 | n/a |
| 2B.28 | | | | | | | | | | | | | | | | | | | | | | | | | N | T | | | | | | | | | | F | | | | | | | 1.1 | 3.2 |
| 2B.35 | | | | | | | | | | | | | | | | | | | | | | | | | T | | | | | | | | | | | M | | | | | | | 1.5 | ~1000 |
| 2B.48 | | | | | | | | | | | | | | | | | | | | | | | | | A | | | | | | | | | | | P | | | | | | | 9.2 | 1.2 |
| 2B.64 | | | | | | | | | | | | | | | | | | | | | | | | | S | | | | | | F | | | | | | | | | | | | ~1000 | 3.5 |
| 2C.75 | | | | | | | | | | | | | | | | | | | | | | | | | F | | | | | | | | | | | | | | | | | V | 0.6 | ~1000 |

Figure 7B

| Clones | IL5 | | | IL4 | | |
|---|---|---|---|---|---|---|
| | $k_{on}(1/Ms)$ | $k_{off}(1/s)$ | $K_D(nM)$ | $k_{on}(1/Ms)$ | $k_{off}(1/s)$ | $K_D(nM)$ |
| E7 | 8.98E+02 | 8.13E-04 | 905.0 | 8.65E+05 | 2.91E-03 | 3.4 |
| 1C36 | 9.18E+03 | 2.21E-04 | 24.1 | 5.57E+05 | 1.97E-03 | 3.5 |
| 1C60 | 1.24E+04 | 5.52E-04 | 44.4 | 6.97E+05 | 3.42E-03 | 4.9 |

Figure 7C

Light chain variable region

| Kabat number | 1 | 2 | 3 | 4 | 5 | 6 | 7 | 8 | 9 | 10 | 11 | 12 | 13 | 14 | 15 | 16 | 17 | 18 | 19 | 20 | 21 | 22 | 23 | 24 | 25 | 26 | 27 | 28 | 29 | 30 | 31 | 32 | 33 | 34 | 35 | 36 | 37 | 38 | 39 | 40 | 41 | 42 |
|---|---|---|---|---|---|---|---|---|---|---|---|---|---|---|---|---|---|---|---|---|---|---|---|---|---|---|---|---|---|---|---|---|---|---|---|---|---|---|---|---|---|---|
| E7   | D | I | Q | M | T | Q | S | P | S | S | L | S | A | S | V | G | D | R | V | T | I | T | C | K | A | S | Q | S | V | I | N | D | A | A | W | Y | Q | Q | K | P | G | K |
| 1C36 | D | I | Q | M | T | Q | S | P | S | S | L | S | A | S | V | G | D | R | V | T | I | T | C | K | A | S | Q | S | V | I | N | D | A | A | W | Y | Q | Q | K | P | G | K |
| 1C60 | D | I | Q | M | T | Q | S | P | S | S | L | S | A | S | V | G | D | R | V | T | I | T | C | K | A | S | Q | S | V | I | N | D | A | A | W | Y | Q | Q | K | P | G | K |

CDR L1 – Contact: positions 24–34 (KASQSVINDAA)

| Kabat number | 43 | 44 | 45 | 46 | 47 | 48 | 49 | 50 | 51 | 52 | 53 | 54 | 55 | 56 | 57 | 58 | 59 | 60 | 61 | 62 | 63 | 64 | 65 | 66 | 67 | 68 | 69 | 70 | 71 | 72 | 73 | 74 | 75 | 76 | 77 | 78 | 79 | 80 | 81 | 82 | 83 | 84 |
|---|---|---|---|---|---|---|---|---|---|---|---|---|---|---|---|---|---|---|---|---|---|---|---|---|---|---|---|---|---|---|---|---|---|---|---|---|---|---|---|---|---|---|
| E7   | A | P | K | L | L | – | – | Y | Y | T | S | H | R | Y | T | G | V | P | S | R | F | S | G | S | G | S | G | T | D | F | T | L | – | S | S | L | Q | P | E | D | F | A |
| 1C36 | A | P | K | L | L | – | – | Y | Y | T | S | H | R | Y | T | G | V | P | S | R | F | S | G | S | G | S | G | T | D | F | T | L | – | S | S | L | Q | P | E | D | F | A |
| 1C60 | A | P | K | L | L | – | – | Y | Y | T | S | H | R | Y | T | G | V | P | S | R | F | S | G | S | G | S | G | T | D | F | T | L | – | S | S | L | Q | P | E | D | F | A |

CDR L2 – Contact: positions 50–56 (YYTSHRY)

| Kabat number | 85 | 86 | 87 | 88 | 89 | 90 | 91 | 92 | 93 | 94 | 95 | 95a | 96 | 97 | 98 | 99 | 100 | 101 | 102 | 103 | 104 | 105 | 106 | |
|---|---|---|---|---|---|---|---|---|---|---|---|---|---|---|---|---|---|---|---|---|---|---|---|---|
| E7   | T | Y | Y | C | Q | Q | D | Y | T | S | P | – | W | T | F | G | Q | G | T | K | V | – | K | SEQ ID No: 1 |
| 1C36 | T | Y | Y | C | Q | Q | D | Y | T | H | P | – | W | T | F | G | Q | G | T | K | V | – | K | SEQ ID No: 29 |
| 1C60 | T | Y | Y | C | Q | Q | D | Y | K | H | P | – | W | T | F | G | Q | G | T | K | V | – | K | SEQ ID No: 33 |

CDR L3 – Contact: positions 89–97

Figure 7D

Heavy chain variable region

| Kabat number | 1 | 2 | 3 | 4 | 5 | 6 | 7 | 8 | 9 | 10 | 11 | 12 | 13 | 14 | 15 | 16 | 17 | 18 | 19 | 20 | 21 | 22 | 23 | 24 | 25 | 26 | 27 | 28 | 29 | 30 | 31 | 32 | 33 | 34 | 35 | 36 | 37 | 38 | 39 | 40 | 41 | 42 |
|---|---|---|---|---|---|---|---|---|---|---|---|---|---|---|---|---|---|---|---|---|---|---|---|---|---|---|---|---|---|---|---|---|---|---|---|---|---|---|---|---|---|---|
| E7   | E | V | Q | L | V | Q | S | G | A | E | V | K | K | P | G | A | S | V | K | V | S | C | K | A | S | G | Y | T | F | T | D | Y | F | I | H | W | V | R | Q | A | P | G |
| 1C36 | E | V | Q | L | V | Q | S | G | A | E | V | K | K | P | G | A | S | V | K | V | S | C | K | A | S | G | Y | T | F | T | D | Y | F | – | H | W | V | R | Q | A | P | G |
| 1C60 | E | V | Q | L | V | Q | S | G | A | E | V | K | V | K | P | G | A | S | V | K | V | S | C | K | A | S | G | Y | T | F | T | D | Y | F | I | H | W | V | R | Q | A | P | G |

CDR H1 – Contact / Kabat

| Kabat number | 43 | 44 | 45 | 46 | 47 | 48 | 49 | 50 | 51 | 52 | 52a | 52b | 53 | 54 | 55 | 56 | 57 | 58 | 59 | 60 | 61 | 62 | 63 | 64 | 65 | 66 | 67 | 68 | 69 | 70 | 71 | 72 | 73 | 74 | 75 | 76 | 77 | 78 | 79 | 80 | 81 | 82 | 82a | 82b | 82c |
|---|---|---|---|---|---|---|---|---|---|---|---|---|---|---|---|---|---|---|---|---|---|---|---|---|---|---|---|---|---|---|---|---|---|---|---|---|---|---|---|---|---|---|---|---|---|
| E7   | Q | G | L | E | W | I | G | G | I | V | Y | D | A | T | G | F | T | T | Y | A | E | E | F | K | G | R | V | T | I | T | R | D | T | S | T | S | T | A | Y | L | E | L | S | S | L |
| 1C36 | Q | G | L | E | W | I | G | G | I | V | Y | D | A | T | G | F | T | T | Y | A | E | E | F | K | G | R | V | T | I | T | R | D | T | S | T | S | T | A | Y | L | E | L | S | S | L |
| 1C60 | Q | G | L | E | W | I | A | G | I | V | Y | Y | D | A | T | G | F | T | W | Y | A | D | D | F | K | G | R | V | T | I | T | R | D | T | S | T | S | T | A | Y | L | E | L | S | S | L |

CDR H2 – Contact / Kabat

| Kabat number | 82c | 83 | 84 | 85 | 86 | 87 | 88 | 89 | 90 | 91 | 92 | 93 | 94 | 95 | 96 | 97 | 98 | 99 | 100 | 100a | 101 | 102 | 103 | 104 | 105 | 106 | 107 | 108 | 109 | 110 | 111 | 112 | 113 | |
|---|---|---|---|---|---|---|---|---|---|---|---|---|---|---|---|---|---|---|---|---|---|---|---|---|---|---|---|---|---|---|---|---|---|---|
| E7   | S | R | S | E | D | T | A | V | Y | Y | C | A | R | G | G | G | I | F | Y | G | M | D | Y | W | G | Q | G | T | L | V | T | V | S | S | SEQ ID No: 4  |
| 1C36 | S | R | S | E | D | T | A | V | Y | Y | C | A | R | G | G | – | – | F | Y | G | M | D | Y | W | G | Q | G | T | L | V | T | V | S | S | SEQ ID No: 30 |
| 1C60 | S | R | S | E | D | T | A | V | Y | Y | C | A | R | G | G | – | I | F | Y | G | M | D | Y | W | G | Q | G | T | L | V | T | V | S | S | SEQ ID No: 34 |

CDR H3 – Contact / Kabat

DUAL SPECIFIC ANTIBODIES FOR BINDING INTERLEUKIN 4 (IL4) AND INTERLEUKIN 5 (IL5)

CROSS-REFERENCE TO RELATED APPLICATIONS

This application is a divisional application of U.S. application Ser. No. 15/167,030, filed on May 27, 2016, which is a continuation application of International Application No. PCT/US2014/071193, filed on Dec. 18, 2014, which claims benefit of the filing date of U.S. Provisional Application No. 61/946,547, filed on Feb. 28, 2014, and U.S. Provisional Application No. 61/919,552, filed on Dec. 20, 2013.

SEQUENCE LISTING

The instant application contains a Sequence Listing which has been submitted electronically in ASCII format and is hereby incorporated by reference in its entirety. Said ASCII copy, created on Apr. 27, 2020, is named _Sequence_Listing_4_27_20_ST25 and is 19,058 bytes in size.

FIELD OF THE INVENTION

The present invention relates to dual specific antibodies, and methods of making and using such antibodies.

BACKGROUND OF THE INVENTION

Antibodies are specific immunoglobulin polypeptides produced by the vertebrate immune system in response to challenge by foreign proteins, glycoproteins, cells, or other antigenic foreign substances. An important part of this process is the generation of antibodies that bind specifically to a particular foreign substance. The binding specificity of such polypeptides to a particular antigen is highly refined, and the multitude of specificities capable of being generated by the individual vertebrate is remarkable in its complexity and variability. Thousands of antigens are capable of eliciting responses, each almost exclusively directed to the particular antigen which elicited it.

Specific antigen recognition is essential for antibodies to function in the adaptive immune response. The combinatorial association of heavy chain (HC) and light chain (LC) is conserved in all vertebrates in the generation of the antibody repertoire. There is, however, asymmetry of diversity in the two chains. The variable domain of HC ($V_H$) contains significantly higher sequence diversity and contributes the determinants of antigen recognition more often than the variable domain of the LC ($V_L$). However, given the variability by which antibodies recognize and bind to a particular foreign substance, some antibodies rely heavily on $V_L$ for antigen-binding energy.

The specificity of antibodies and antibody fragments for a particular antigen or antigens makes antibodies desirable therapeutic agents. Antibodies and antibody fragments can be used to target particular antigens with pleiotropic biological roles (e.g., cytokines). As such, there is a current and continuing need to identify and characterize therapeutic antibodies, especially antibodies, fragments, and derivatives thereof, useful in the treatment of various diseases and disorders, such as allergic diseases, inflammatory diseases, autoimmune diseases, and proliferative diseases.

SUMMARY OF THE INVENTION

The present invention provides methods of making dual specific antibodies and antibody fragments. The invention also provides specific antibodies identified using these methods as well as their use.

In general, the methods of the invention involve diversifying the $V_H$ of an antibody to generate dual specific antibody variants that can be stably expressed in a library. In one embodiment, the antibody, prior to being diversified, is characterized as having a $V_H$ and a $V_L$ that pair together to form an antigen binding site that specifically binds to a first epitope but not a second epitope. The antibody is further characterized as having an electrostatic or hydrophobic residue at any one, two, or three of the amino acids found at positions 32, 50, or 91 (Kabat numbering system) of the $V_L$. Such an antibody, having a hydrophobic or electrostatic residue at one or more of these positions, is then altered at one or more amino acid residues (e.g., solvent exposed amino acid residues) in the $V_H$. The $V_H$ and $V_L$ may then be expressed (e.g., as a library) and diversified dual specific antibodies, or antigen-binding fragments thereof, that are capable of specifically binding to the first and second epitope are selected from the expressed $V_H$ and $V_L$.

In one aspect, the invention features a method of making a dual specific antibody, or antigen-binding fragment thereof, comprising a variable heavy chain domain ($V_H$) and a variable light chain domain ($V_L$), wherein the $V_H$ and $V_L$ of the dual specific antibody pair together to form an antigen-binding site that specifically binds to a first epitope and a second epitope, said method comprising the steps of: (a) providing an antibody that comprises a $V_H$ and $V_L$, wherein the $V_H$ and $V_L$ pair together to form an antigen-binding site that binds to a first epitope but not the second epitope and wherein said antibody comprises at least one amino acid at position 32, 50, or 91 of the $V_L$ that is electrostatic or hydrophobic; (b) altering the nucleic acid sequence encoding the $V_H$ of the antibody of step (a), wherein one or more solvent accessible amino acid residues are altered; (c) expressing $V_L$ and the altered $V_H$ of step (b); and (d) selecting a dual specific antibody, or antigen-binding fragment thereof, comprising the $V_L$ and the altered $V_H$ of step (c), wherein the $V_H$ and $V_L$ pair together to form an antigen binding site that specifically binds to the first epitope and the second epitope.

In some embodiments, at least two of the amino acids at position 32, 50, or 91 are electrostatic or hydrophobic. In some embodiments, all three amino acids at position 32, 50 and 91 are electrostatic or hydrophobic. In some embodiments, the electrostatic residue is a tyrosine. In some embodiments, the hydrophobic residue is a tryptophan. In some embodiments, the nucleic acid sequence encoding the $V_H$ is altered based on the diversity of a plurality of naturally occurring heavy chain amino acid sequences. In some embodiments, the solvent exposed residue position is an amino acid residue position selected from the group consisting of positions 33, 34, 50-58, and 95-97 of the $V_H$. In some embodiments, the method further comprises altering the nucleic acid sequence encoding the $V_L$ of the antibody of step (a), wherein one or more solvent accessible amino acid residues are altered. In some embodiments, the solvent exposed residue position is an amino acid residue position selected from amino acids 93-96 of the $V_L$. In some embodiments, the altered $V_H$ are displayed on phage with the $V_L$ during the selection of step (d). In some embodiments, the antibody of step (a) comprises a light chain variable region complementarity determining region CDRL1 comprising the amino acid sequence KASQSVINDAA (SEQ ID NO: 9), a CDRL2 comprising the amino acid sequence YTSHRYT (SEQ ID NO: 10), and a CDRL3 comprising the amino acid sequence QQDYTSPWTF (SEQ ID NO: 11). In some embodiments, the antibody of step (a) comprises a heavy chain variable region complementarity determining region CDRH1 comprising the amino acid sequence DYSMH (SEQ ID NO: 13), a CDRH2 comprising the amino acid sequence VWINTETGEPTYADDFK (SEQ ID NO: 17), and a CDRH3 comprising the amino acid sequence GGI-FYGMDY (SEQ ID NO: 20). In some embodiments, the antigen binding site of the dual specific antibody of step (d) binds the first epitope and second epitope mutually exclusively. In other embodiments, the antigen binding site of the dual specific antibody of step (d) binds the first epitope and second epitope simultaneously. In some embodiments, the first epitope is from one biological molecule and the second epitope is from the same biological molecule. In other embodiments, the first epitope is from a first biological molecule and the second epitope is from a second biological molecule. In some embodiments, the first biological molecule and the second biological molecule are selected from the group consisting of IL4/IL5 and IL4/IL13. In some embodiments, the first biological molecule and the second biological molecule are cytokines. In some embodiments, the first or the second biological molecule is a molecule which can increase the half life of the dual specific antibody when bound to the antibody in vivo. In some embodiments, the first or the second biological molecule is serum albumin or a neonatal Fc receptor (FcRn). In some embodiments, the first or the second biological molecule is a molecule which can increase the effector function of a dual specific antibody when bound to the antibody in vivo. In some embodiments, the first or the second biological molecule binds to a cell surface protein on natural killer cells or macrophages. In some embodiments, the cell surface protein is an Fc receptor or C1q. In some embodiments, the $V_H$ and $V_L$ of the dual specific antibody pair together to form an antigen binding site that specifically binds to the first epitope or the second epitope with a $K_D$ of $10^{-6}$ or lower. In some embodiments, the $V_H$ and $V_L$ of the dual specific antibody pair together to form an antigen binding site that specifically binds to the first epitope or the second epitope with a $K_D$ of $10^{-9}$ or lower. In some embodiments, the $V_H$ and $V_L$ of the dual specific antibody pair together to form an antigen binding site that specifically binds to the first epitope or the second epitope with a $K_D$ of $10^{-12}$ or lower. In some embodiments, the $V_H$ and $V_L$ of the dual specific antibody pair together to form an antigen binding site that specifically binds to the first epitope and the second epitope with a $K_D$ of $10^{-6}$ or lower. In some embodiments, the $V_H$ and $V_L$ of the dual specific antibody pair together to form an antigen binding site that specifically binds to the first epitope and the second epitope with a $K_D$ of $10^{-9}$ or lower. In some embodiments, the $V_H$ and $V_L$ of the dual specific antibody pair together to form an antigen binding site that specifically binds to the first epitope and the second epitope with a $K_D$ of $10^{-12}$ or lower. In some embodiments, the first biological molecule and the second biological molecule are not structurally similar. In some embodiments, the selecting of step (d) comprises deep sequencing, ultra-deep sequencing, and/or next generation sequencing.

Exemplary antibodies produced using the methods of the invention include antibodies that bind both interleukin 4 (IL4) and interleukin 5 (IL5), as well as antibodies that bind both IL4 and interleukin 13 (IL13), as described below. Successful production of these antibodies demonstrates that altering the sequence of the heavy chain variable domain of an antibody can serve as a general engineering path toward generating antibodies with dual specificity and function. The dual specific antibodies, including but not limited to the IL4/IL5 and IL4/IL13 antibodies described herein, have the potential to simultaneously target two pathways (redundant or non-redundant) and are useful for the treatment of various diseases and disorders including, but not limited to, immune disorders, inflammatory disorders, and proliferative disorders.

Accordingly, in another aspect, the invention features an isolated dual specific antibody, or antigen-binding fragment thereof, made by the method of the invention described above. In some embodiments, the dual specific antibody is a monoclonal antibody. In some embodiments, the fragment is a Fab or a scFv. In some embodiments, the dual specific antibody is an IgG.

In another aspect, the invention features an isolated dual specific antibody, or antigen-binding fragment thereof, that comprises the amino acid sequence of any one of the antibodies of FIG. 4A, 4B, 4C, 7A, 7C, or 7D.

In another aspect, the invention features an isolated dual specific antibody, or antigen-binding fragment thereof, comprising the following six CDRs: (i) a CDRL1 comprising the amino acid sequence of KASQSVINDAA (SEQ ID NO: 9); (ii) a CDRL2 comprising the amino acid sequence of YTSHRYT (SEQ ID NO: 10); (iii) a CDRL3 comprising the amino acid sequence of QQDYTSPWTF (SEQ ID NO: 11); (iv) a CDRH1 comprising the amino acid sequence of DYDIH (SEQ ID NO: 14); (v) a CDRH2 comprising the amino acid sequence of VWINTETGEPTYADDFK (SEQ ID NO: 17); and (vi) a CDRH3 comprising the amino acid sequence of EILFYGMDY (SEQ ID NO: 21).

In another aspect, the invention features an isolated dual specific antibody, or antigen-binding fragment thereof, comprising the following six CDRs: (i) a CDRL1 comprising the amino acid sequence of KASQSVINDAA (SEQ ID NO: 9); (ii) a CDRL2 comprising the amino acid sequence of YTSHRYT (SEQ ID NO: 10); (iii) a CDRL3 comprising the amino acid sequence of QQDYTSPWTF (SEQ ID NO: 11); (iv) a CDRH1 comprising the amino acid sequence of DYFIH (SEQ ID NO: 15); (v) a CDRH2 comprising the amino acid sequence of AGIVYDATGFTTYADDFK (SEQ ID NO: 18); and (vi) a CDRH3 comprising the amino acid sequence of GGIFYGMDY (SEQ ID NO: 20).

In another aspect, the invention features an isolated dual specific antibody, or antigen-binding fragment thereof, comprising the following six CDRs: (i) a CDRL1 comprising the amino acid sequence of KASQSVINDAA (SEQ ID NO: 9); (ii) a CDRL2 comprising the amino acid sequence of YTSHRYT (SEQ ID NO: 10); (iii) a CDRL3 comprising the amino acid sequence of QQDYTPFPLTF (SEQ ID NO: 12); (iv) a CDRH1 comprising the amino acid sequence of DYLMH (SEQ ID NO: 16); (v) a CDRH2 comprising the amino acid sequence of AVIVSITGRTYYADDFK (SEQ ID NO: 19); and (vi) a CDRH3 comprising the amino acid sequence of GGIFYGMDY (SEQ ID NO: 20).

In another aspect, the invention features an isolated dual specific antibody, or antigen-binding fragment thereof, comprising the following six CDRs: (i) a CDRL1 comprising the amino acid sequence of KASQSVINDAA (SEQ ID NO: 9); (ii) a CDRL2 comprising the amino acid sequence of YTSHRYT (SEQ ID NO: 10); (iii) a CDRL3 comprising the amino acid sequence of QQDYTSPWTF (SEQ ID NO: 11); (iv) a CDRH1 comprising the amino acid sequence of DYSMH (SEQ ID NO: 13); (v) a CDRH2 comprising the amino acid sequence of GVIFQSGATYYADDFK (SEQ ID NO: 22); and (vi) a CDRH3 comprising the amino acid sequence of GGIFYGMDY (SEQ ID NO: 20).

In another aspect, the invention features an isolated dual specific antibody, or antigen-binding fragment thereof, comprising the following six CDRs: (i) a CDRL1 comprising the amino acid sequence of KASQSVINDAA (SEQ ID NO: 9); (ii) a CDRL2 comprising the amino acid sequence of YTSHRYT (SEQ ID NO: 10); (iii) a CDRL3 comprising the amino acid sequence of QQDYTSPWTF (SEQ ID NO: 11); (iv) a CDRH1 comprising the amino acid sequence of DYSMH (SEQ ID NO: 13); (v) a CDRH2 comprising the amino acid sequence of GIIFYTGHTYYADDFK (SEQ ID NO: 23); and (vi) a CDRH3 comprising the amino acid sequence of GGIFYGMDY (SEQ ID NO: 20).

In another aspect, the invention features an isolated dual specific antibody, or antigen-binding fragment thereof, comprising the following six CDRs: (i) a CDRL1 comprising the amino acid sequence of KASQSVINDAA (SEQ ID NO: 9); (ii) a CDRL2 comprising the amino acid sequence of YTSHRYT (SEQ ID NO: 10); (iii) a CDRL3 comprising the amino acid sequence of QQDYX$_1$X$_2$PWTF (SEQ ID NO: 24), wherein X$_1$ is Thr, Ile, Leu, or Lys, and X$_2$ is Ser or His; (iv) a CDRH1 comprising the amino acid sequence of DYFIH (SEQ ID NO: 15); (v) a CDRH2 comprising the amino acid sequence of X$_1$GIVYDATGFTX$_2$YA X$_3$X$_4$FK (SEQ ID NO: 25), wherein X$_1$ is Ala or Gly, X$_2$ is Thr, Ile, Val, or Ala, X$_3$ is Asp, Val, or Glu, and X$_4$ is Asp, Glu, Asn, Ser, Ile, Leu, Thr, Ala, or Phe; and (vi) a CDRH3 comprising the amino acid sequence of GGIFYGMDY (SEQ ID NO: 20). In some embodiments, the dual specific antibody, or antigen-binding fragment thereof, comprises the following six CDRs: (i) a CDRL1 comprising the amino acid sequence of KASQSVINDAA (SEQ ID NO: 9); (ii) a CDRL2 comprising the amino acid sequence of YTSHRYT (SEQ ID NO: 10); (iii) a CDRL3 comprising the amino acid sequence of QQDYTHPWTF (SEQ ID NO: 27); (iv) a CDRH1 comprising the amino acid sequence of DYFIH (SEQ ID NO: 15); (v) a CDRH2 comprising the amino acid sequence of GGIVYDATGFTTYAEEFK (SEQ ID NO: 28); and (vi) a CDRH3 comprising the amino acid sequence of GGIFYGMDY (SEQ ID NO: 20). In some embodiments, the dual specific antibody, or antigen-binding fragment thereof, comprises the following six CDRs: (i) a CDRL1 comprising the amino acid sequence of KASQSVINDAA (SEQ ID NO: 9); (ii) a CDRL2 comprising the amino acid sequence of YTSHRYT (SEQ ID NO: 10); (iii) a CDRL3 comprising the amino acid sequence of QQDYKHPWTF (SEQ ID NO: 31); (iv) a CDRH1 comprising the amino acid sequence of DYFIH (SEQ ID NO: 15); (v) a CDRH2 comprising the amino acid sequence of AGIVYDATGFTVYADDFK (SEQ ID NO: 32); and (vi) a CDRH3 comprising the amino acid sequence of GGIFYGMDY (SEQ ID NO: 20). In some embodiments, the dual specific antibody, or antigen-binding fragment thereof, further comprises a framework region 3 (FR3) comprising the amino acid sequence of GRX$_1$TITX$_2$DX$_3$STSTX$_4$(SEQ ID NO: 26), wherein X$_1$ is Val or Phe, X$_2$ is Arg or Ile, X$_3$ is Thr, Phe, Met, or Pro, and X$_4$ is Ala or Val.

In another aspect, the invention features an isolated dual specific antibody, or antigen-binding fragment thereof, comprising a light chain variable region selected from the amino acid sequence of SEQ ID NOs: 1, 5, 29, or 33, and a heavy chain variable region selected from SEQ ID NOs: 2, 3, 4, 6, 7, 8, 30, or 34. In some embodiments, the antibody, or antigen-binding fragment thereof, binds IL4 with a Kd of 500 nM or lower and IL5 with a Kd of about 900 nM or lower. In some embodiments, the antibody, or antigen-binding fragment thereof, binds IL4 with a Kd of 100 nM or lower and IL5 with a Kd of about 100 nM or lower. In some embodiments, the antibody, or antigen-binding fragment thereof, binds IL4 with a Kd of 10 nM or lower and IL5 with a Kd of about 50 nM or lower. In other embodiments, the isolated dual specific antibody, or antigen-binding fragment thereof, binds IL4 with a Kd of 500 nM or lower and IL13 with a Kd of about 900 nM or lower. In some embodiments, the antibody, or antigen-binding fragment thereof, binds IL4 with a Kd of 100 nM or lower and IL13 with a Kd of about 100 nM or lower. In some embodiments, the antibody, or antigen-binding fragment thereof, inhibits or blocks binding of IL4, IL5 or IL13 to its receptor. In some embodiments, the antibody is a monoclonal antibody. In some embodiments, the antibody is an IgG antibody. In some embodiments, the antigen-binding fragment is a Fab fragment or a single chain variable fragment (scFv). In some embodiments, at least a portion of the framework sequence is a human consensus framework sequence. In some embodiments, the antibody is a chimeric, humanized, or fully human antibody.

Also provided is a pharmaceutical composition comprising any one of the preceding dual specific antibodies, or antigen-binding fragments thereof. In another aspect, the invention features an isolated nucleic acid that encodes any of the dual specific antibodies disclosed herein, comprising a vector (e.g., an expression vector) for expressing the antibody.

In another aspect, the invention features host cells comprising the preceding nucleic acids and/or vectors. In some embodiments, the host cell is a mammalian cell (e.g., a Chinese hamster ovary (CHO) cell). In other embodiments, the host cell is a prokaryotic cell (e.g., an *E. coli* cell). A method of producing any one of the preceding dual specific antibodies is also provided, the method comprising culturing the host cell that produces the dual specific antibody and recovering the dual specific antibody from the host cell or the culture medium.

In another aspect, the invention features a method of treating asthma in a subject, the method comprising administering to the subject any of the dual specific antibodies disclosed herein, wherein the administering is for a time and in an amount sufficient to treat or prevent the asthma in the subject. In some embodiments, the method further comprises administering at least one additional asthma treatment selected from the group consisting of an IgE antagonist, an anti-histamine, theophylline, salbutamol, beclomethasone dipropionate, sodium cromoglycate, a steroid, and an anti-inflammatory agents. In some embodiments, the asthma is allergic asthma.

In yet another aspect, the invention features a method of treating a proliferative disorder in a subject, the method comprising administering to the subject any of the dual specific antibodies disclosed herein, wherein the administering is for a time and in an amount sufficient to treat proliferative disorder in the subject. In some embodiments, the proliferative disorder is cancer. In some embodiments, the method further comprises administering to the subject an additional anti-proliferative agent selected from the group consisting of a chemotherapeutic agent, a cytotoxic agent, and an anti-angiogenic agent.

Figures 1A, 1B:
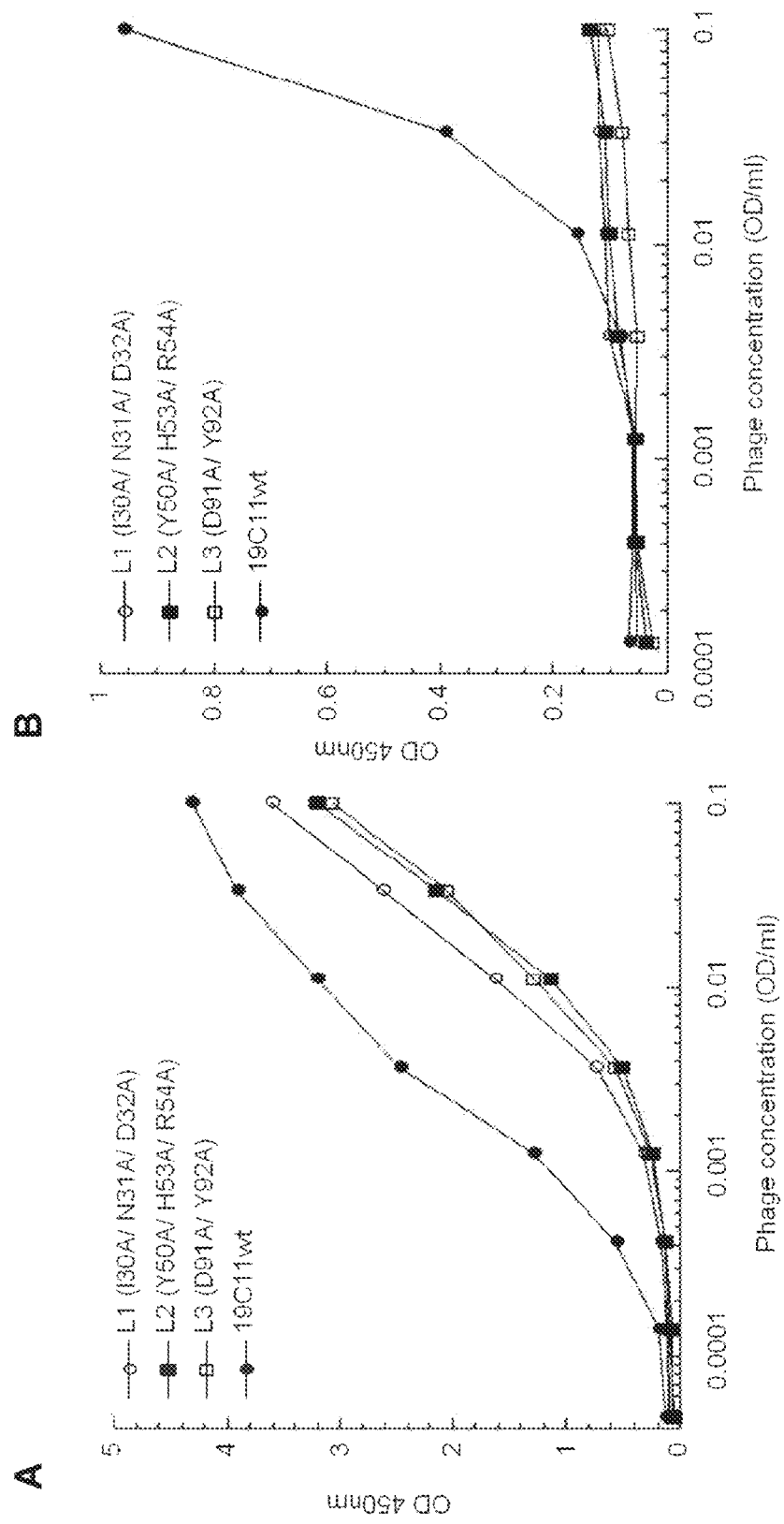
FIGS. 1A and 1B are graphs showing mutagenesis mapping of hu19C11 antibody CDRs. To measure the relative antigen binding affinity of hu19C11 Fab variants, binding of serially diluted phage displaying anti-IL4 hu19C11 wild type (wt) or LC CDR alanine mutants to anti-gD antibody (A) or IL4 (B) coated on ELISA wells was detected by Fab expression and an anti-M13 phage horseradish peroxidase (HRP) conjugate to quantify antigen binding, respectively. gD is an expression peptide tag fused to the C terminus of the light chain. Anti-gD antibody was directly coated on ELISA wells, whereas IL4 was captured with a non-blocking anti-IL4 antibody coated on ELISA wells.

In general, the methods of the invention involve diversifying the $V_H$ of an antibody to generate variants that can be stably expressed in a library. In general, an antibody, which specifically binds to a first epitope but not a second epitope and which is characterized as having an electrostatic or hydrophobic residue at any one, two, or three of the amino acids found at positions 32, 50, or 91 (in Kabat numbering) of the $V_L$ is altered at one or more amino acid residues (e.g., solvent exposed amino acid residues) in the $V_H$. The $V_H$ and $V_L$ are then expressed and diversified dual specific antibodies, or antigen-binding fragments thereof, that are capable of specifically binding to the first and second epitope are then selected from the expressed $V_H$ and $V_L$.

Exemplary antibodies produced using the methods of the invention include antibodies that bind both interleukin 4 (IL4) and interleukin 5 (IL5), as well as antibodies that bind both IL4 and interleukin 13 (IL13), as described below. These antibodies demonstrate that mutations in the heavy chain variable domain (e.g., the CDRs) of an IL4 antibody confer dual binding capabilities for additional, unrelated proteins as well as IL4 and provide proof of concept for the general strategy of altering residues in the $V_H$ to confer dual specificity. The dual specific antibodies, including but not limited to the IL4/IL5 and IL4/IL13 antibodies, described herein, have the potential to simultaneously target multiple antigens, for example, the redundant and non-redundant pathways of cytokines, rendering them useful for the treatment of various diseases and disorders, including cytokine-mediated diseases (e.g., asthma).

I. Definitions

The term "multispecific antibody" is used in the broadest sense and specifically covers an antibody comprising a heavy chain variable domain ($V_H$) and a light chain variable domain ($V_L$), where the $V_H V_L$ unit has polyepitopic specificity (i.e., is capable of binding to two different epitopes on one biological molecule or each epitope on a different biological molecule). Such multispecific antibodies include, but are not limited to, full-length antibodies, antibodies having two or more $V_L$ and $V_H$ domains, antibody fragments such as Fab, Fv, dsFv, scFv, diabodies, bispecific diabodies and triabodies, antibody fragments that have been linked covalently or non-covalently. "Polyepitopic specificity" refers to the ability to specifically bind to two or more different epitopes on the same or different target(s). "Dual specificity" or "bispecificity" refers to the ability to specifically bind to two different epitopes on the same or different target(s). However, in contrast to bispecific antibodies, dual-specific antibodies are natural IgG antibodies in format, wherein the two antigen-binding arms are identical in amino acid sequence and each Fab arm is capable of recognizing two antigens. Dual-specificity allows the antibodies to interact with high affinity with two different antigens as a single Fab or IgG molecule. According to one embodiment, the multispecific antibody in an IgG1 form binds to each epitope with an affinity of 5 µM to 0.001 pM, 3 pM to 0.001 pM, 1 µM to 0.001 pM, 0.5 µM to 0.001 pM or 0.1 µM to 0.001 pM. "Monospecific" refers to the ability to bind only one epitope.

In general, an antibody includes a basic 4-chain antibody unit which is a heterotetrameric glycoprotein composed of two identical light (L) chains and two identical heavy (H) chains (an IgM antibody consists of 5 of the basic heterotetramer units along with an additional polypeptide called J chain, and therefore contains 10 antigen binding sites, while secreted IgA antibodies can polymerize to form polyvalent assemblages comprising 2-5 of the basic 4-chain units along with J chain). In the case of IgGs, the 4-chain unit is generally about 150,000 Daltons. Each L chain is linked to an H chain by one covalent disulfide bond, while the two H chains are linked to each other by one or more disulfide bonds depending on the H chain isotype. Each H and L chain also has regularly spaced intrachain disulfide bridges. Each H chain has, at the N-terminus, a variable domain ($V_H$) followed by three constant domains ($C_H$) for each of the α and γ chains and four CH domains for µ and ε isotypes. Each L chain has, at the N-terminus, a variable domain ($V_L$) followed by a constant domain ($C_L$) at its other end. The $V_L$ is aligned with the $V_H$ and the $C_L$ is aligned with the first constant domain of the heavy chain ($C_H 1$). Particular amino acid residues are believed to form an interface between the light chain and heavy chain variable domains. The pairing of a $V_H$ and $V_L$ together forms an antigen-binding site. For the structure and properties of the different classes of antibodies, see, e.g., *Basic and Clinical Immunology*, 8th edition, Daniel P. Stites, Abba I. Terr and Tristram G. Parslow (eds.), Appleton & Lange, Norwalk, C T, 1994, page 71 and Chapter 6. The L chain from any vertebrate species can be assigned to one of two clearly distinct types, called kappa and lambda, based on the amino acid sequences of their constant domains. Depending on the amino acid sequence of the constant domain of their heavy chains ($C_H$), immunoglobulins can be assigned to different classes or isotypes. There are five classes of immunoglobulins: IgA, IgD, IgE, IgG, and IgM, having heavy chains designated α, δ, γ, ε, and µ, respectively. The γ and α classes are further divided into subclasses on the basis of relatively minor differences in $C_H$ sequence and function, e.g., humans express the following subclasses: IgG1, IgG2, IgG3, IgG4, IgA1, and IgA2.

The term "variable" refers to the fact that certain segments of the variable domains differ extensively in sequence among antibodies. The variable or "V" domain mediates antigen binding and defines specificity of a particular antibody for its particular antigen. However, the variability is not evenly distributed across the 110-amino acid span of the variable domains. Instead, the V regions consist of relatively invariant stretches called framework regions (FRs) of 15-30 amino acids separated by shorter regions of extreme variability called "hypervariable regions" that are each 9-12 amino acids long. The variable domains of native heavy and light chains each comprise four FRs, largely adopting a beta-sheet configuration, connected by three hypervariable regions, which form loops connecting, and in some cases forming part of, the beta-sheet structure. The hypervariable regions in each chain are held together in close proximity by the FRs and, with the hypervariable regions from the other chain, contribute to the formation of the antigen-binding site of antibodies (see Kabat et al., *Sequences of Proteins of Immunological Interest*, 5th Ed. Public Health Service, National Institutes of Health, Bethesda, MD. (1991)). The constant domains are not involved directly in binding an antibody to an antigen, but exhibit various effector functions, such as participation of the antibody in antibody dependent cellular cytotoxicity (ADCC).

The term "hypervariable region" when used herein refers to the amino acid residues of an antibody which are responsible for antigen-binding. The hypervariable region generally comprises amino acid residues from a "complementarity determining region" or "CDR" (e.g., around about residues 24-34 (L1), 50-56 (L2) and 89-97 (L3) in the $V_L$, and around about residues 26-35 (H1), 49-65 (H2) and 95-102 (H3) in the $V_H$ (in one embodiment, H1 is around about residues 31-35); Kabat et al., *Sequences of Proteins of Immunological Interest,* 5th Ed. Public Health Service, National Institutes of Health, Bethesda, MD. (1991)) and/or those residues from a "hypervariable loop" (e.g., residues 26-32 (L1), 50-52 (L2), and 91-96 (L3) in the $V_L$, and 26-32 (H1), 53-55 (H2), and 96-101 (H3) in the $V_H$; Chothia and Lesk, J. Mol. Biol. 196:901-917 (1987)).

The term "monoclonal antibody" as used herein refers to an antibody from a population of substantially homogeneous antibodies, i.e., the individual antibodies comprising the population are substantially similar and bind the same epitope(s), except for possible variants that may arise during production of the monoclonal antibody, such variants generally being present in minor amounts. Such monoclonal antibody typically includes an antibody comprising a variable region that binds a target, wherein the antibody was obtained by a process that includes the selection of the antibody from a plurality of antibodies. For example, the selection process can be the selection of a unique clone from a plurality of clones, such as a pool of hybridoma clones, phage clones or recombinant DNA clones. It should be understood that the selected antibody can be further altered, for example, to improve affinity for the target, to humanize the antibody, to improve its production in cell culture, to reduce its immunogenicity in vivo, to create a multispecific antibody, etc., and that an antibody comprising the altered variable region sequence is also a monoclonal antibody of this invention. In addition to their specificity, the monoclonal antibody preparations are advantageous in that they are typically uncontaminated by other immunoglobulins. The modifier "monoclonal" indicates the character of the antibody as being obtained from a substantially homogeneous population of antibodies, and is not to be construed as requiring production of the antibody by any particular method. For example, the monoclonal antibodies to be used in accordance with the present invention may be made by a variety of techniques, including the hybridoma method (e.g., Kohler et al., Nature, 256:495 (1975); Harlow et al., Antibodies: A Laboratory Manual, (Cold Spring Harbor Laboratory Press, 2nd ed. 1988); Hammerling et al., in: Monoclonal Antibodies and T-Cell Hybridomas 563-681, (Elsevier, N.Y., 1981), recombinant DNA methods (see, e.g., U.S. Pat. No. 4,816,567), phage display technologies (see, e.g., Clackson et al., Nature, 352:624-628 (1991); Marks et al., J. Mol. Biol., 222:581-597 (1991); Sidhu et al., J. Mol. Biol. 338(2):299-310 (2004); Lee et al., J. Mol. Biol. 340 (5):1073-1093 (2004); Fellouse, Proc. Nat. Acad. Sci. USA 101(34):12467-12472 (2004); and Lee et al. J. Immunol. Methods 284(1-2):119-132 (2004) and technologies for producing human or human-like antibodies from animals that have parts or all of the human immunoglobulin loci or genes encoding human immunoglobulin sequences (see, e.g., WO98/24893, WO/9634096, WO/9633735, and WO/91 10741, Jakobovits et al., Proc. Natl. Acad. Sci. USA, 90:2551 (1993); Jakobovits et al., Nature, 362:255-258 (1993); Bruggemann et al., Year in Immuno., 7:33 (1993); U.S. Pat. Nos. 5,545,806, 5,569,825, 5,591,669 (all of GenPharm); 5,545,807; WO 97/17852, U.S. Pat. Nos. 5,545, 807; 5,545,806; 5,569,825; 5,625,126; 5,633,425; and 5,661,016, and Marks et al., Bio/Technology, 10: 779-783 (1992); Lonberg et al., Nature, 368: 856-859 (1994); Morrison, Nature, 368: 812-813 (1994); Fishwild et al., Nature Biotechnology, 14: 845-851 (1996); Neuberger, Nature Biotechnology, 14: 826 (1996); and Lonberg and Huszar, Intern. Rev. Immunol., 13: 65-93 (1995).

The monoclonal antibodies herein specifically include chimeric, humanized, fully human, and affinity matured antibodies. Chimeric antibodies are antibodies in which a portion of the heavy and/or light chain is identical with or homologous to corresponding sequences in antibodies derived from a particular species or belonging to a particular antibody class or subclass, while the remainder of the chain(s) is identical with or homologous to corresponding sequences in antibodies derived from another species or belonging to another antibody class or subclass, as well as fragments of such antibodies, so long as they exhibit the desired biological activity (U.S. Pat. No. 4,816,567; and Morrison et al., Proc. Natl. Acad. Sci. USA, 81:6851-6855 (1984)). Chimeric antibodies of interest herein include "primatized" antibodies comprising variable domain antigen-binding sequences derived from a non-human primate (e.g. Old World Monkey, Ape etc) and human constant region sequences.

"Humanized" forms of non-human (e.g., rodent) antibodies are chimeric antibodies that contain minimal sequence derived from the non-human antibody. For the most part, humanized antibodies are human immunoglobulins (recipient antibody) in which residues from a hypervariable region of the recipient are replaced by residues from a hypervariable region of a non-human species (donor antibody) such as mouse, rat, rabbit or non-human primate having the desired antibody specificity, affinity, and capability. In some instances, framework region (FR) residues of the human immunoglobulin are replaced by corresponding non-human residues. Furthermore, humanized antibodies can comprise residues that are not found in the recipient antibody or in the donor antibody. These modifications are made to further refine antibody performance. In general, the humanized antibody will comprise substantially all of at least one, and typically two, variable domains, in which all or substantially all of the hypervariable loops correspond to those of a non-human immunoglobulin and all or substantially all of the FRs are those of a human immunoglobulin sequence. The humanized antibody optionally also will comprise at least a portion of an immunoglobulin constant region (Fc), typically that of a human immunoglobulin. For further details, see Jones et al., Nature 321:522-525 (1986); Riechmann et al., Nature 332:323-329 (1988); and Presta, Curr. Op. Struct. Biol. 2:593-596 (1992).

A "human antibody" is one which possesses an amino acid sequence which corresponds to that of an antibody produced by a human and/or has been made using any of the techniques for making human antibodies. This definition of a human antibody specifically excludes a humanized antibody comprising non-human antigen-binding residues.

An "affinity matured" antibody is one with one or more alterations in one or more CDRs thereof which result in an improvement in the affinity of the antibody for antigen, compared to a parent antibody which does not possess those alteration(s). Preferred affinity matured antibodies will have nanomolar or even picomolar affinities for the target antigen. Affinity matured antibodies are produced by procedures known in the art. Marks et al. Bio/Technology 10:779-83 (1992) describes affinity maturation by $V_H$ and $V_L$ domain shuffling. Random mutagenesis of CDR and/or framework residues is described by: Barbas et al., Proc Nat. Acad. Sci. USA 91:3809-13 (1994); Schier et al. Gene 169:147-55 (1995); Yelton et al., J. Immunol. 155:1994-2004 (1995); Jackson et al., J. Immunol. 154(7):3310-19 (1995); and Hawkins et al., J. Mol. Biol. 226:889-96 (1992).

An "intact" antibody is one which comprises an antigen-binding site as well as a $C_L$ and at least heavy chain constant domains, $C_H1$, $C_H2$, and $C_H3$. The constant domains can be native sequence constant domains (e.g., human native sequence constant domains) or amino acid sequence variant thereof. Preferably, the intact antibody has one or more effector functions.

"Antibody fragments" comprise a portion of an intact antibody, preferably the antigen binding or variable region of the intact antibody. Examples of antibody fragments include Fab, Fab', F(ab')$_2$, and Fv fragments; diabodies; linear antibodies (see U.S. Pat. No. 5,641,870, Example 2; Zapata et al., Protein Eng. 8(10): 1057-1062 (1995)); single-chain antibody molecules; and multispecific antibodies formed from antibody fragments.

The expression "linear antibodies" generally refers to the antibodies described in Zapata et al., Protein Eng., 8(10): 1057-1062 (1995). Briefly, these antibodies comprise a pair of tandem Fd segments ($V_H$-$C_H1$-$V_H$-$C_H1$) which, together with complementary light chain polypeptides, form a pair of antigen binding regions. Linear antibodies can be bispecific or monospecific.

Papain digestion of antibodies produces two identical antigen-binding fragments, called "Fab" fragments, and a residual "Fc" fragment, a designation reflecting the ability to crystallize readily. The Fab fragment consists of an entire L chain along with the variable region domain of the H chain ($V_H$), and the first constant domain of one heavy chain ($C_H1$). Pepsin treatment of an antibody yields a single large F(ab')$_2$ fragment which roughly corresponds to two disulfide linked Fab fragments having divalent antigen-binding activity and is still capable of cross-linking antigen. Fab' fragments differ from Fab fragments by having additional few residues at the carboxy terminus of the $C_H1$ domain including one or more cysteines from the antibody hinge region. Fab'-SH is the designation herein for Fab' in which the cysteine residue(s) of the constant domains bear a free thiol group. F(ab')$_2$ antibody fragments originally were produced as pairs of Fab' fragments which have hinge cysteines between them. Other chemical couplings of antibody fragments are also known.

The Fc fragment comprises the carboxy-terminal portions of both H chains held together by disulfides. The effector functions of antibodies are determined by sequences in the Fc region; this region is also the part recognized by Fc receptors (FcR) found on certain types of cells.

"Fv" consists of a dimer of one heavy- and one light-chain variable region domain in tight, non-covalent association. From the folding of these two domains emanate six hypervariable loops (3 loops each from the H and L chain) that contribute the amino acid residues for antigen binding and confer antigen binding specificity to the antibody. However, even a single variable domain (or half of an Fv comprising only three CDRs specific for an antigen) has the ability to recognize and bind antigen, although often at a lower affinity than the entire binding site.

"Single-chain Fv" also abbreviated as "sFv" or "scFv" are antibody fragments that comprise the $V_H$ and $V_L$ antibody domains connected into a single polypeptide chain. Preferably, the sFv polypeptide further comprises a polypeptide linker between the $V_H$ and $V_L$ domains which enables the sFv to form the desired structure for antigen binding. For a review of sFv, see Pluckthun in *The Pharmacology of Monoclonal Antibodies*, vol. 113, Rosenburg and Moore eds., Springer-Verlag, New York, pp. 269-315 (1994); Borrebaeck 1995.

The term "diabodies" refers to small antibody fragments prepared by constructing sFv fragments (see preceding paragraph) with short linkers (about 5-10 residues) between the $V_H$ and $V_L$ domains such that inter-chain but not intra-chain pairing of the V domains is achieved, resulting in a bivalent fragment, i.e., fragment having two antigen-binding sites. Bispecific diabodies are heterodimers of two "crossover" sFv fragments in which the $V_H$ and $V_L$ domains of the two antibodies are present on different polypeptide chains. Diabodies are described more fully in, for example, EP 404,097; WO 93/11161; and Hollinger et al., Proc. Natl. Acad. Sci. USA, 90:6444-6448 (1993).

By "electrostatic" is meant having a charge. Generally, electrostatic amino acids have polar or charged side chains. Examples of amino acids with polar side chains include serine, threonine, tyrosine, cysteine, asparagine, and glutamine. Examples of amino acids with negatively charged side chains include aspartic acid, and glutamic acid. Examples of amino acids with positively charged side chains include lysine, arginine, and histidine.

By "hydrophobic" is meant not compatible with water or not dissolving in, absorbing, or mixing easily with water. Generally, hydrophobic amino acids have non-polar side chains and examples include alanine, glycine, isoleucine, leucine, methionine, phenylalanine, proline, tryptophan, and valine.

The term "cytokine" is a generic term for proteins released by one cell population which act on another cell as intercellular mediators. Examples of cytokines include lymphokines, monokines, and traditional polypeptide hormones. Included among the cytokines are growth hormones such as human growth hormone, N-methionyl human growth hormone, and bovine growth hormone; parathyroid hormone; thyroxine; insulin and proinsulin; relaxin and prorelaxin; glycoprotein hormones such as follicle stimulating hormone (FSH), thyroid stimulating hormone (TSH), and luteinizing hormone (LH); hepatic growth factor; fibroblast growth factor; prolactin; placental lactogen; tumor necrosis factor-α and -β; mullerian-inhibiting substance; mouse gonadotropin-associated peptide; inhibin; activin; vascular endothelial growth factor; integrin; thrombopoietin (TPO); nerve growth factors such as NGF-β; platelet-growth factor; transforming growth factors (TGFs) such as TGF-α and TGF-β; insulin-like growth factor-I and -II; erythropoietin (EPO); osteoinductive factors; interferons such as interferon-α, -β, and -γ; colony stimulating factors (CSFs) such as macrophage-CSF (M-CSF); granulocyte-macrophage-CSF (GM-CSF); and granulocyte-CSF (G-CSF); interleukins (ILs) such as IL1, IL1α, IL2, IL3, IL4, IL5, IL6, IL7, IL8, IL11, IL12, and IL13; a tumor necrosis factor such as TNF-α or TNF-β; and other polypeptide factors including LIF and kit ligand (KL). As used herein, the term cytokine includes proteins from natural sources or from recombinant cell culture and biologically active equivalents of the native sequence cytokines.

As used herein, "codon set" refers to a set of different nucleotide triplet sequences used to encode desired variant amino acids. A set of oligonucleotides can be synthesized, for example, by solid phase synthesis, including sequences that represent all possible combinations of nucleotide triplets provided by the codon set and that will encode the desired group of amino acids. A standard form of codon designation is that of the IUB code, which is known in the art and described herein. A codon set typically is represented by 3 capital letters in italics, e.g., NNK, NNS, XYZ, DVK, and the like (e.g., NNKcodon refers to N=A/T/G/C at positions 1 and 2 in the codon and K=G/T at equimolar ratio in position 3 to encode all 20 natural amino acids). A "non-random codon set," as used herein, thus refers to a codon set that encodes select amino acids that fulfill partially, preferably completely, the criteria for amino acid selection as described herein. Synthesis of oligonucleotides with selected nucleotide "degeneracy" at certain positions is well known in that art, for example the TRIM approach (Knappek et al., J. Mol. Biol. 296:57-86, 1999); Garrard and Henner, Gene 128:103, 1993). Such sets of oligonucleotides having certain codon sets can be synthesized using commercial nucleic acid synthesizers (available from, for example, Applied Biosystems, Foster City, CA), or can be obtained commercially (for example, from Life Technologies, Rockville, MD). Therefore, a set of oligonucleotides synthesized having a particular codon set will typically include a plurality of oligonucleotides with different sequences, the differences established by the codon set within the overall sequence. Oligonucleotides, as used according to the invention, have sequences that allow for hybridization to a variable domain nucleic acid template and also can, but do not necessarily, include restriction enzyme sites useful for, for example, cloning purposes.

An antibody of this invention "which binds" an antigen of interest is one that binds the antigen with sufficient affinity such that the antibody is useful as a diagnostic and/or therapeutic agent in targeting a protein or a cell or tissue expressing the antigen, and does not significantly cross-react with other proteins. In such embodiments, the extent of binding of the antibody to a "non-target" protein will be less than about 10% of the binding of the antibody to its particular target protein as determined by fluorescence activated cell sorting (FACS) analysis or radioimmunoprecipitation (RIA) or ELISA. With regard to the binding of a antibody to a target molecule, the term "specific binding" or "specifically binds to" or is "specific for" a particular polypeptide or an epitope on a particular polypeptide target means binding that is measurably different from a non-specific interaction. Specific binding can be measured, for example, by determining binding of a molecule compared to binding of a control molecule. For example, specific binding can be determined by competition with a control molecule that is similar to the target, for example, an excess of non-labeled target. In this case, specific binding is indicated if the binding of the labeled target to a probe is competitively inhibited by excess unlabeled target. The term "specific binding" or "specifically binds to" or is "specific for" a particular polypeptide or an epitope on a particular polypeptide target as used herein can be exhibited, for example, by a molecule having a $K_D$ for the target of $10^{-4}$ M or lower, alternatively $10^{-5}$ M or lower, alternatively $10^{-6}$ M or lower, alternatively $10^{-7}$ M or lower, alternatively $10^{-8}$ M or lower, alternatively $10^{-8}$ M or lower, alternatively $10^{-10}$ M or lower, alternatively $10^{-11}$ M or lower, alternatively $10^{-12}$ M or lower or a $K_D$ in the range of $10^{-4}$ M to $10^{-12}$ M or $10^{-6}$ M to $10^{-10}$ M or $10^{-7}$ M to $10^{-9}$ M. As will be appreciated by the skilled artisan, affinity and $K_D$ values are inversely related. A high affinity for an antigen is measured by a low $K_D$ value. In one embodiment, the term "specific binding" refers to binding where a molecule binds to a particular polypeptide or epitope on a particular polypeptide without substantially binding to any other polypeptide or polypeptide epitope.

"Biologically active" and "biological activity" and "biological characteristics" with respect to a polypeptide of this invention means having the ability to bind to a biological molecule, except where specified otherwise.

"Biological molecule" refers to a nucleic acid, a protein, a carbohydrate, a lipid, and combinations thereof. In one embodiment, the biologic molecule exists in nature.

"Isolated," when used to describe the various antibodies disclosed herein, means an antibody that has been identified and separated and/or recovered from a cell or cell culture from which it was expressed. Contaminant components of its natural environment are materials that would typically interfere with diagnostic or therapeutic uses for the polypeptide, and can include enzymes, hormones, and other proteinaceous or non-proteinaceous solutes. In preferred embodiments, the antibody will be purified (1) to a degree sufficient to obtain at least 15 residues of N-terminal or internal amino acid sequence by use of a spinning cup sequenator, or (2) to homogeneity by SDS-PAGE under non-reducing or reducing conditions using Coomassie blue or, preferably, silver stain. Isolated antibody includes antibodies in situ within recombinant cells, because at least one component of the polypeptide natural environment will not be present. Ordinarily, however, isolated polypeptide will be prepared by at least one purification step.

The term "control sequences" refers to DNA sequences necessary for the expression of an operably linked coding sequence in a particular host organism. The control sequences that are suitable for prokaryotes, for example, include a promoter, optionally an operator sequence, and a ribosome binding site. Eukaryotic cells are known to utilize promoters, polyadenylation signals, and enhancers.

Nucleic acid is "operably linked" when it is placed into a functional relationship with another nucleic acid sequence. For example, DNA for a presequence or secretory leader is operably linked to DNA for a polypeptide if it is expressed as a preprotein that participates in the secretion of the polypeptide; a promoter or enhancer is operably linked to a coding sequence if it affects the transcription of the sequence; or a ribosome binding site is operably linked to a coding sequence if it is positioned so as to facilitate translation. Generally, "operably linked" means that the DNA sequences being linked are contiguous, and, in the case of a secretory leader, contiguous and in reading phase. However, enhancers do not have to be contiguous. Linking is accomplished by ligation at convenient restriction sites. If such sites do not exist, the synthetic oligonucleotide adaptors or linkers are used in accordance with conventional practice.

"Percent (%) amino acid sequence identity" with respect to the polypeptide sequences identified herein is defined as the percentage of amino acid residues in a candidate sequence that are identical with the amino acid residues in the polypeptide being compared, after aligning the sequences and introducing gaps, if necessary, to achieve the maximum percent sequence identity, and not considering any conservative substitutions as part of the sequence identity. Alignment for purposes of determining percent amino acid sequence identity can be achieved in various ways that are within the skill in the art, for instance, using publicly available computer software such as BLAST, BLAST-2, ALIGN or Megalign (DNASTAR) software. Those skilled in the art can determine appropriate parameters for measuring alignment, including any algorithms needed to achieve maximal alignment over the full-length of the sequences being compared. For purposes herein, however, % amino acid sequence identity values are generated using the sequence comparison computer program ALIGN-2. The ALIGN-2 sequence comparison computer program was authored by Genentech, Inc. and the source code has been filed with user documentation in the U.S. Copyright Office, Washington D.C., 20559, where it is registered under U.S. Copyright Registration No. TXU510087. The ALIGN-2 program is publicly available through Genentech, Inc., South San Francisco, California. The ALIGN-2 program should be compiled for use on a UNIX operating system, preferably digital UNIX V4.0D. All sequence comparison parameters are set by the ALIGN-2 program and do not vary.

The amino acid sequences described herein are contiguous amino acid sequences unless otherwise specified.

"Structurally unsimilar" biological molecules according to this invention refers to biological molecules that are not in the same class (protein, nucleic acid, lipid, carbohydrates, etc.) or, for example, when referring to proteins, having less than 60% amino acid identity, less than 50% amino acid identity, less than 40% amino acid identity, less than 30% amino acid identity, less than 20% amino acid identity or less than 10% amino acid identity compared to each other.

"Stringency" of hybridization reactions is readily determinable by one of ordinary skill in the art, and generally is an empirical calculation dependent upon probe length, washing temperature, and salt concentration. In general, longer probes require higher temperatures for proper annealing, while shorter probes need lower temperatures. Hybridization generally depends on the ability of denatured DNA to reanneal when complementary strands are present in an environment below their melting temperature. The higher the degree of desired homology between the probe and hybridizable sequence, the higher the relative temperature which can be used. As a result, it follows that higher relative temperatures would tend to make the reaction conditions more stringent, while lower temperatures less so. For additional details and explanation of stringency of hybridization reactions, see Ausubel et al., *Current Protocols in Molecular Biology*, Wiley Interscience Publishers, (1995).

"Stringent conditions" or "high stringency conditions," as defined herein, can be identified by those that: (1) employ low ionic strength and high temperature for washing, for example 0.015 M sodium chloride/0.0015 M sodium citrate/0.1% sodium dodecyl sulfate at 50C; (2) employ during hybridization a denaturing agent, such as formamide, for example, 50% (v/v) formamide with 0.1% bovine serum albumin/0.1% Ficoll/0.1% polyvinylpyrrolidone/50 mM sodium phosphate buffer at pH 6.5 with 750 mM sodium chloride, 75 mM sodium citrate at 42° C.; or (3) overnight hybridization in a solution that employs 50% formamide, 5×SSC (0.75 M NaCl, 0.075 M sodium citrate), 50 mM sodium phosphate (pH 6.8), 0.1% sodium pyrophosphate, 5×Denhardt's solution, sonicated salmon sperm DNA (50 µg/ml), 0.1% SDS, and 10% dextran sulfate at 42° C., with a 10 minute wash at 42° C. in 0.2×SSC (sodium chloride/sodium citrate) followed by a 10 minute high-stringency wash consisting of 0.1×SSC containing EDTA at 55° C.

"Moderately stringent conditions" can be identified as described by Sambrook et al., *Molecular Cloning: A Laboratory Manual*, New York: Cold Spring Harbor Press, 1989, and include the use of washing solution and hybridization conditions (e.g., temperature, ionic strength, and % SDS) less stringent that those described above. An example of moderately stringent conditions is overnight incubation at 37° C. in a solution comprising: 20% formamide, 5×SSC (150 mM NaCl, 15 mM trisodium citrate), 50 mM sodium phosphate (pH 7.6), 5×Denhardt's solution, 10% dextran sulfate, and 20 mg/ml denatured sheared salmon sperm DNA, followed by washing the filters in 1×SSC at about 37-50° C. The skilled artisan will recognize how to adjust the temperature, ionic strength, etc. as necessary to accommodate factors such as probe length and the like.

Antibody "effector functions" refer to those biological activities attributable to the Fc region (a native sequence Fc region or amino acid sequence variant Fc region) of an antibody, and vary with the antibody isotype. Examples of antibody effector functions include: C1q binding and complement dependent cytotoxicity; Fc receptor binding; antibody-dependent cell-mediated cytotoxicity (ADCC); phagocytosis; down regulation of cell surface receptors (e.g., B cell receptor); and B cell activation.

"Antibody-dependent cell-mediated cytotoxicity" or "ADCC" refers to a form of cytotoxicity in which secreted Ig bound onto Fc receptors (FcRs) present on certain cytotoxic cells (e.g., Natural Killer (NK) cells, neutrophils, and macrophages) enable these cytotoxic effector cells to bind specifically to an antigen-bearing target cell and subsequently kill the target cell with cytotoxins. The antibodies "arm" the cytotoxic cells and are absolutely required for such killing. The primary cells for mediating ADCC, NK cells, express FcγRIII only, whereas monocytes express FcγRI, FcγRII, and FcγRIII. FcR expression on hematopoietic cells is summarized in Table 3 on page 464 of Ravetch and Kinet, Annu. Rev. Immunol. 9:457-92 (1991). To assess ADCC activity of a molecule of interest, an in vitro ADCC assay, such as that described in U.S. Pat. No. 5,500,362 or 5,821,337 can be performed. Useful effector cells for such assays include peripheral blood mononuclear cells (PBMC) and Natural Killer (NK) cells. Alternatively, or additionally, ADCC activity of the molecule of interest can be assessed in vivo, e.g., in a animal model such as that disclosed in Clynes et al. (Proc. Natl. Acad. Sci. USA) 95:652-656 (1998).

"Fc receptor" or "FcR" describes a receptor that binds to the Fc region of an antibody. The preferred FcR is a native sequence human FcR. Moreover, a preferred FcR is one which binds an IgG antibody (a gamma receptor) and includes receptors of the FcγRI, FcγRII, and FcγRIII subclasses, including allelic variants and alternatively spliced forms of these receptors. FcγRII receptors include FcγRIIA (an "activating receptor") and FcγRIIB (an "inhibiting receptor"), which have similar amino acid sequences that differ primarily in the cytoplasmic domains thereof. Activating receptor FcγRIIA contains an immunoreceptor tyrosine-based activation motif (ITAM) in its cytoplasmic domain. Inhibiting receptor FcγRIIB contains an immunoreceptor tyrosine-based inhibition motif (ITIM) in its cytoplasmic domain (see review M. in Daëron, Annu. Rev. Immunol. 15:203-234 (1997)). FcRs are reviewed in Ravetch and Kinet, (Annu. Rev. Immunol. 9:457-492 (1991)); Capel et al., (Immunomethods 4:25-34 (1994)); and de Haas et al., (J. Lab. Clin. Med. 126:330-41 (1995)). Other FcRs, including those to be identified in the future, are encompassed by the term "FcR" herein. The term also includes the neonatal receptor, FcRn, which is responsible for the transfer of maternal IgGs to the fetus (Guyer et al., J. Immunol. 117:587 (1976) and Kim et al., J. Immunol. 24:249 (1994)).

"Human effector cells" are leukocytes which express one or more FcRs and perform effector functions. Preferably, the cells express at least FcγRIII and perform ADCC effector function. Examples of human leukocytes which mediate ADCC include peripheral blood mononuclear cells (PBMC), natural killer (NK) cells, monocytes, cytotoxic T cells, and neutrophils; with PBMCs and NK cells being preferred. The effector cells can be isolated from a native source, e.g., from blood.

"Complement dependent cytotoxicity" or "CDC" refers to the lysis of a target cell in the presence of complement. Activation of the classical complement pathway is initiated by the binding of the first component of the complement system (C1q) to antibodies (of the appropriate subclass) which are bound to their cognate antigen. To assess complement activation, a CDC assay, e.g., as described in Gazzano-Santoro et al., J. Immunol. Methods 202:163 (1996), can be performed.

The term "therapeutically effective amount" refers to an amount of an antibody or antibody fragment to treat a disease or disorder in a subject. In the case of an allergic, inflammatory, or autoimmune disease (e.g., asthma, arthritis, etc.), the therapeutically effective amount of the antibody or antibody fragment (e.g., a dual specific or multispecific antibody or antibody fragment for IL4 and IL5 or IL4 and IL13) may ameliorate or treat the disease, or prevent, reduce, ameliorate, or treat symptoms associated with the disease. In the case of a proliferative disease (e.g., a cancerous tumor), the therapeutically effective amount of the antibody or antibody fragment may reduce the number of cancer cells; reduce the primary tumor size; inhibit (i.e., slow to some extent and preferably stop) cancer cell infiltration into peripheral organs; inhibit (i.e., slow to some extent and preferably stop) tumor metastasis; inhibit, to some extent, tumor growth; and/or relieve to some extent one or more of the symptoms associated with the disorder. To the extent the antibody or antibody fragment may prevent growth and/or kill existing cancer cells, it may be cytostatic and/or cytotoxic. For cancer therapy, efficacy in vivo can, for example, be measured by assessing the duration of survival, time to disease progression (TTP), duration of disease free survival (DFS), duration of progression free survival (PFS), the response rates (RR), duration of response, and/or quality of life.

By "reduce or inhibit" is meant the ability to cause an overall decrease preferably of 20% or greater, more preferably of 50% or greater, and most preferably of 75%, 85%, 90%, 95%, or greater. Reduce or inhibit can refer to the symptoms of the disorder being treated, the presence or size of metastases, the size of the primary tumor, or the size or number of the blood vessels in angiogenic disorders.

An "inflammatory disease" as used herein refers to pathological states resulting in inflammation, typically caused by neutrophil chemotaxis.

An "autoimmune disease" as used herein is a disease or disorder arising from and directed against an individual's own tissues, or a co-segregate or manifestation thereof, or resulting condition therefrom.

Examples of diseases or disorders that are inflammatory, autoimmune, or both, include, but are not limited to, asthma such as asthma bronchiale, bronchial asthma, and autoimmune asthma, arthritis (rheumatoid arthritis such as acute arthritis, chronic rheumatoid arthritis, gouty arthritis, acute gouty arthritis, chronic inflammatory arthritis, degenerative arthritis, infectious arthritis, Lyme arthritis, proliferative arthritis, psoriatic arthritis, vertebral arthritis, and juvenile-onset rheumatoid arthritis, osteoarthritis, arthritis chronica progrediente, arthritis deformans, polyarthritis chronica primaria, reactive arthritis, and ankylosing spondylitis), inflammatory hyperproliferative skin diseases, psoriasis such as plaque psoriasis, gutatte psoriasis, pustular psoriasis, and psoriasis of the nails, dermatitis including contact dermatitis, chronic contact dermatitis, allergic dermatitis, allergic contact dermatitis, dermatitis herpetiformis, and atopic dermatitis, x-linked hyper IgM syndrome, urticaria such as chronic allergic urticaria and chronic idiopathic urticaria, including chronic autoimmune urticaria, polymyositis/dermatomyositis, juvenile dermatomyositis, toxic epidermal necrolysis, scleroderma (including systemic scleroderma), sclerosis such as systemic sclerosis, multiple sclerosis (MS) such as spino-optical MS, primary progressive MS (PPMS), and relapsing remitting MS (RRMS), progressive systemic sclerosis, atherosclerosis, arteriosclerosis, sclerosis disseminata, and ataxic sclerosis, inflammatory bowel disease (IBD) (for example, Crohn's disease, autoimmune-mediated gastrointestinal diseases, colitis such as ulcerative colitis, colitis ulcerosa, microscopic colitis, collagenous colitis, colitis polyposa, necrotizing enterocolitis, and transmural colitis, and autoimmune inflammatory bowel disease), pyoderma gangrenosum, erythema nodosum, primary sclerosing cholangitis, episcleritis), respiratory distress syndrome, including adult or acute respiratory distress syndrome (ARDS), meningitis, inflammation of all or part of the uvea, iritis, choroiditis, an autoimmune hematological disorder, rheumatoid spondylitis, sudden hearing loss, IgE-mediated diseases such as anaphylaxis and allergic and atopic rhinitis, hyper IgE syndrome, encephalitis such as Rasmussen's encephalitis and limbic and/or brainstem encephalitis, uveitis, such as anterior uveitis, acute anterior uveitis, granulomatous uveitis, nongranulomatous uveitis, phacoantigenic uveitis, posterior uveitis, or autoimmune uveitis, glomerulonephritis (GN) with and without nephrotic syndrome such as chronic or acute glomerulonephritis such as primary GN, immune-mediated GN, membranous GN (membranous nephropathy), idiopathic membranous GN or idiopathic membranous nephropathy, membrano- or membranous proliferative GN (MPGN), including Type I and Type II, and rapidly progressive GN, allergic conditions, allergic reaction, eczema including allergic or atopic eczema, scleroderma, Whipple's disease, hypertrophic scarring, pre-eclampsia, abdominal adhesions, conditions involving infiltration of T cells and chronic inflammatory responses, chronic pulmonary inflammatory disease, autoimmune myocarditis, leukocyte adhesion deficiency, systemic lupus erythematosus (SLE) or systemic lupus erythematodes such as cutaneous SLE, subacute cutaneous lupus erythematosus, neonatal lupus syndrome (NLE), lupus erythematosus disseminatus, lupus (including nephritis, cerebritis, pediatric, non-renal, extra-renal, discoid, alopecia), juvenile onset (Type I) diabetes mellitus, including pediatric insulin-dependent diabetes mellitus (IDDM), adult onset diabetes mellitus (Type II diabetes), autoimmune diabetes, idiopathic diabetes insipidus, immune responses associated with acute and delayed hypersensitivity mediated by cytokines and T-lymphocytes, tuberculosis, sarcoidosis, granulomatosis including lymphomatoid granulomatosis, Wegener's granulomatosis, agranulocytosis, vasculitides, including vasculitis (including large vessel vasculitis (including polymyalgia rheumatica and giant cell (Takayasu's) arteritis), medium vessel vasculitis (including Kawasaki's disease and polyarteritis nodosa), microscopic polyarteritis, CNS vasculitis, necrotizing, cutaneous, or hypersensitivity vasculitis, systemic necrotizing vasculitis, and ANCA-associated vasculitis, such as Churg-Strauss vasculitis or syndrome (CSS)), temporal arteritis, aplastic anemia, autoimmune aplastic anemia, Coombs positive anemia, Diamond Blackfan anemia, hemolytic anemia or immune hemolytic anemia including autoimmune hemolytic anemia (AIHA), pernicious anemia (anemia perniciosa), Addison's disease, pure red cell anemia or aplasia (PRCA), Factor VIII deficiency, hemophilia A, autoimmune neutropenia, pancytopenia, leukopenia, diseases involving leukocyte diapedesis, CNS inflammatory disorders, multiple organ injury syndrome such as those secondary to septicemia, trauma or hemorrhage, antigen-antibody complex-mediated diseases, anti-glomerular basement membrane disease, anti-phospholipid antibody syndrome, allergic neuritis, Bechet's or Behcet's disease, Castleman's syndrome, Goodpasture's syndrome, Reynaud's syndrome, Sjogren's syndrome, Stevens-Johnson syndrome, pemphigoid such as pemphigoid bullous and skin pemphigoid, pemphigus (including pemphigus vulgaris, pemphigus foliaceus, pemphigus mucus-membrane pemphigoid, and pemphigus erythematosus), autoimmune polyendocrinopathies, Reiter's disease or syndrome, immune complex nephritis, antibody-mediated nephritis, neuromyelitis optica, polyneuropathies, chronic neuropathy such as IgM polyneuropathies or IgM-mediated neuropathy, thrombocytopenia (as developed by myocardial infarction patients, for example), including thrombotic thrombocytopenic purpura (TTP) and autoimmune or immune-mediated thrombocytopenia such as idiopathic thrombocytopenic purpura (ITP) including chronic or acute ITP, autoimmune disease of the testis and ovary including autoimmune orchitis and oophoritis, primary hypothyroidism, hypoparathyroidism, autoimmune endocrine diseases including thyroiditis such as autoimmune thyroiditis, Hashimoto's disease, chronic thyroiditis (Hashimoto's thyroiditis), or subacute thyroiditis, autoimmune thyroid disease, idiopathic hypothyroidism, Grave's disease, polyglandular syndromes such as autoimmune polyglandular syndromes (or polyglandular endocrinopathy syndromes), paraneoplastic syndromes, including neurologic paraneoplastic syndromes such as Lambert-Eaton myasthenic syndrome or Eaton-Lambert syndrome, stiff-man or stiff-person syndrome, encephalomyelitis such as allergic encephalomyelitis or encephalomyelitis allergica and experimental allergic encephalomyelitis (EAE), myasthenia gravis such as thymoma-associated myasthenia gravis, cerebellar degeneration, neuromyotonia, opsoclonus or opsoclonus myoclonus syndrome (OMS), and sensory neuropathy, multifocal motor neuropathy, Sheehan's syndrome, autoimmune hepatitis, chronic hepatitis, lupoid hepatitis, giant cell hepatitis, chronic active hepatitis or autoimmune chronic active hepatitis, lymphoid interstitial pneumonitis, bronchiolitis obliterans (non-transplant) vs NSIP, Guillain-Barré syndrome, Berger's disease (IgA nephropathy), idiopathic IgA nephropathy, linear IgA dermatosis, primary biliary cirrhosis, pneumonocirrhosis, autoimmune enteropathy syndrome, Celiac disease, celiac sprue (gluten enteropathy), refractory sprue, idiopathic sprue, cryoglobulinemia, amylotrophic lateral sclerosis (ALS; Lou Gehrig's disease), coronary artery disease, autoimmune ear disease such as autoimmune inner ear disease (AIED), autoimmune hearing loss, opsoclonus myoclonus syndrome (OMS), polychondritis such as refractory or relapsed polychondritis, pulmonary alveolar proteinosis, amyloidosis, scleritis, a non-cancerous lymphocytosis, a primary lymphocytosis, which includes monoclonal B cell lymphocytosis (e.g., benign monoclonal gammopathy and monoclonal garnmopathy of undetermined significance, MGUS), peripheral neuropathy, paraneoplastic syndrome, channelopathies such as epilepsy, migraine, arrhythmia, muscular disorders, deafness, blindness, periodic paralysis, and channelopathies of the CNS, autism, inflammatory myopathy, focal segmental glomerulosclerosis (FSGS), endocrine ophthalmopathy, uveoretinitis, chorioretinitis, autoimmune hepatological disorder, fibromyalgia, multiple endocrine failure, Schmidt's syndrome, adrenalitis, gastric atrophy, presenile dementia, demyelinating diseases such as autoimmune demyelinating diseases, diabetic nephropathy, Dressler's syndrome, alopecia areata, CREST syndrome (calcinosis, Raynaud's phenomenon, esophageal dysmotility, sclerodactyly, and telangiectasia), male and female autoimmune infertility, mixed connective tissue disease, Chagas' disease, rheumatic fever, recurrent abortion, farmer's lung, erythema multiforme, post-cardiotomy syndrome, Cushing's syndrome, bird-fancier's lung, allergic granulomatous angiitis, benign lymphocytic angiitis, Alport's syndrome, alveolitis such as allergic alveolitis and fibrosing alveolitis, interstitial lung disease, transfusion reaction, leprosy, malaria, leishmaniasis, kypanosomiasis, schistosomiasis, ascariasis, aspergillosis, Sampter's syndrome, Caplan's syndrome, dengue, endocarditis, endomyocardial fibrosis, diffuse interstitial pulmonary fibrosis, interstitial lung fibrosis, idiopathic pulmonary fibrosis, cystic fibrosis, endophthalmitis, erythema elevatum et diutinum, erythroblastosis fetalis, eosinophilic faciitis, Shulman's syndrome, Felty's syndrome, flariasis, cyclitis such as chronic cyclitis, heterochronic cyclitis, iridocyclitis, or Fuch's cyclitis, Henoch-Schonlein purpura, human immunodeficiency virus (HIV) infection, echovirus infection, cardiomyopathy, Alzheimer's disease, parvovirus infection, rubella virus infection, post-vaccination syndromes, congenital rubella infection, Epstein-Barr virus infection, mumps, Evan's syndrome, autoimmune gonadal failure, Sydenham's chorea, post-streptococcal nephritis, thromboangitis ubiterans, thyrotoxicosis, tabes dorsalis, chorioiditis, giant cell polymyalgia, endocrine ophthamopathy, chronic hypersensitivity pneumonitis, keratoconjunctivitis sicca, epidemic keratoconjunctivitis, idiopathic nephritic syndrome, minimal change nephropathy, benign familial and ischemia-reperfusion injury, retinal autoimmunity, joint inflammation, bronchitis, chronic obstructive airway disease, silicosis, aphthae, aphthous stomatitis, arteriosclerotic disorders, aspermiogenese, autoimmune hemolysis, Boeck's disease, cryoglobulinemia, Dupuytren's contracture, endophthalmia phacoanaphylactica, enteritis allergica, erythema nodosum leprosum, idiopathic facial paralysis, chronic fatigue syndrome, febris rheumatica, Hamman-Rich's disease, sensoneural hearing loss, haemoglobinuria paroxysmatica, hypogonadism, ileitis regionalis, leucopenia, mononucleosis infectiosa, traverse myelitis, primary idiopathic myxedema, nephrosis, ophthalmia symphatica, orchitis granulomatosa, pancreatitis, polyradiculitis acuta, pyoderma gangrenosum, Quervain's thyreoiditis, acquired spenic atrophy, infertility due to antispermatozoan antobodies, non-malignant thymoma, vitiligo, SCID and Epstein-Barr virus-associated diseases, acquired immune deficiency syndrome (AIDS), parasitic diseases such as Lesihmania, toxic-shock syndrome, food poisoning, conditions involving infiltration of T cells, leukocyte-adhesion deficiency, immune responses associated with acute and delayed hypersensitivity mediated by cytokines and T-lymphocytes, diseases involving leukocyte diapedesis, multiple organ injury syndrome, antigen-antibody complex-mediated diseases, antiglomerular basement membrane disease, allergic neuritis, autoimmune polyendocrinopathies, oophoritis, primary myxedema, autoimmune atrophic gastritis, sympathetic ophthalmia, rheumatic diseases, mixed connective tissue disease, nephrotic syndrome, insulitis, polyendocrine failure, peripheral neuropathy, autoimmune polyglandular syndrome type I, adult-onset idiopathic hypoparathyroidism (AOIH), alopecia totalis, dilated cardiomyopathy, epidermolisis bullosa acquisita (EBA), hemochromatosis, myocarditis, nephrotic syndrome, primary sclerosing cholangitis, purulent or nonpurulent sinusitis, acute or chronic sinusitis, ethmoid, frontal, maxillary, or sphenoid sinusitis, an autoimmune blistering disease, an eosinophil-related disorder such as eosinophilia, idiopathic hypereosinophil syndrome, pulmonary infiltration eosinophilia, eosinophilia-myalgia syndrome, Loffler's syndrome, chronic eosinophilic pneumonia, tropical pulmonary eosinophilia, bronchopneumonic aspergillosis, aspergilloma, or granulomas containing eosinophils, anaphylaxis, seronegative spondyloarthritides, polyendocrine autoimmune disease, sclerosing cholangitis, sclera, episclera, chronic mucocutaneous candidiasis, Bruton's syndrome, transient hypogammaglobulinemia of infancy, Wiskott-Aldrich syndrome, ataxia telangiectasia, autoimmune disorders associated with collagen disease, rheumatism, neurological disease, ischemic re-perfusion disorder, reduction in blood pressure response, vascular dysfunction, antgiectasis, tissue injury, cardiovascular ischemia, hyperalgesia, cerebral ischemia, and disease accompanying vascularization, allergic hypersensitivity disorders, glomerulonephritides, reperfusion injury, reperfusion injury of myocardial or other tissues, dermatoses with acute inflammatory components, acute purulent meningitis or other central nervous system inflammatory disorders, ocular and orbital inflammatory disorders, granulocyte transfusion-associated syndromes, cytokine-induced toxicity, acute serious inflammation, chronic intractable inflammation, pyelitis, pneumonocirrhosis, diabetic retinopathy, diabetic large-artery disorder, endarterial hyperplasia, peptic ulcer, valvulitis, and endometriosis.

An "allergic disease" herein is a disease or disorder in which an individual is hypersensitized to, and mounts an immunologic reaction against, a substance that is normally non-immunogenic. Allergic disease is generally characterized by activation of mast cells by IgE, resulting in an inflammatory response that can result in symptoms as benign as a runny nose, to life-threatening anaphylactic shock and death. Examples of allergic disease include, but are not limited to, asthma (e.g., allergic asthma), allergic rhinitis (e.g., hay fever), allergic dermatitis (e.g., eczema), contact dermatitis, food allergy, and urticaria.

The above list is not all-inclusive, and it will be understood by the skilled artisan that a disease or disorder may fall within various categories. For example, asthma is both an allergic and inflammatory disorder and considered by some clinicians to be an autoimmune disorder.

The terms "cancer" and "cancerous" refer to or describe the physiological condition in mammals that is typically characterized by unregulated cell growth. Included in this definition are benign and malignant cancers.

The term "precancerous" refers to a condition or a growth that typically precedes or develops into a cancer.

The term "proliferative disease" as used herein is a disease or disorder that is associated with some degree of abnormal cell proliferation. In one embodiment, the cell proliferative disorder is cancer. In some embodiments, the cancer is selected from the group consisting of breast cancer, colorectal cancer, non-small cell lung cancer, non-Hodgkin's lymphoma (NHL), B cell lymphoma, B cell leukemia, multiple myeloma, renal cancer, prostate cancer, liver cancer, head and neck cancer, melanoma, ovarian cancer, mesothelioma, and glioblastoma.

The term "tumor" as used herein refers to all neoplastic cell growth and proliferation, whether malignant or benign, and all pre-cancerous and cancerous cells and tissues.

By "non-metastatic" is meant a cancer that is benign or that remains at the primary site and has not penetrated into the lymphatic or blood vessel system or to tissues other than the primary site. Generally, a non-metastatic cancer is any cancer that is a Stage 0, I, or II cancer, and occasionally a Stage III cancer.

A "subject" is a vertebrate, preferably a mammal, more preferably a human. Mammals include, but are not limited to, farm animals (such as cows), sport animals, pets (such as cats, dogs and horses), primates, mice, and rats.

II. Generation of Dual Specific Antibodies

The heavy chain variable domain ($V_H$) contains significantly higher sequence diversity and contributes the determinants of antigen recognition more often than the light chain variable domain ($V_L$). Our previous results demonstrated, for the first time, that the light chain variable domain could be altered to produce a single antibody with dual specificity (see US Patent Application Publication No. 20080069820 and Bostrom et al., Science 232:1610-1614 (2009), herein incorporated by reference in their entirety). We have discovered that dual specific antibodies can be generated from antibodies which have $V_L$ residues that are critical for antigen recognition by alteration of amino acid residues in the $V_H$, including in the absence of mutation to the $V_L$. These novel and unexpected methods are described in detail below.

We have discovered that specific residues can be identified in the $V_L$ which, when electrostatic or hydrophobic, suggests that the $V_L$ is critical for antigen recognition. In such cases, alteration of the $V_H$ of the antibody is used to generate a dual specific antibody that binds to both a first epitope and a second epitope. Specifically, if any one, two, or three of the amino acid residues at positions 32, 50, or 91 (in Kabat numbering) of an antibody are electrostatic (e.g., tyrosine) or hydrophobic (e.g., tryptophan), then the nucleic acid sequence encoding the $V_H$ of that antibody is altered at one or more codons of the $V_H$ that encode one or more solvent accessible amino acid residues.

In various embodiments, the residues in the $V_H$ that may be altered to include any one or more of amino acids 33, 34, 50-58, or 95-97. Optionally, amino acid residues 93-96 of the light chain may be altered in addition to the heavy chain residues. The solvent accessibility or importance for antigen recognition may be determined for the heavy chain using standard techniques known in the art including but not limited to structural mapping and alanine scanning mutagenesis.

The $V_L$ and altered $V_H$ are then expressed (e.g., as a library) and a dual specific antibody, or antigen-binding fragment thereof, that includes a $V_L$ and an altered $V_H$ is selected that specifically binds to a first epitope and a second epitope. The $V_L$ of the initial antibody may or may not be altered in addition to the $V_H$. Amino acid residues in the framework region of the initial antibody may or may not be altered in addition to the $V_H$.

A dual specific antibody, or antigen-binding fragment thereof, that is identified through the selection methods above may be further modified by, for example, affinity maturation or other art known methods, to increase affinity for one or both target antigens. The affinity maturation selection process may include the application of a massive parallel sequencing approach (e.g., deep sequencing, ultra-deep sequencing, or next generation sequencing) to identify residue(s) (e.g., solvent exposed or non-solvent exposed residues) that contribute to the binding of one or both target antigens (e.g., contribute to increased target antigen affinity). See, for example, Fowler et al. *Nat. Methods.* 7(9): 741-746, 2010. The dual specific antibody may also be modified to increase stability or half-life, or to decrease immunogenicity. Such modifications are known to the skilled artisan.

III. Therapeutic Uses

The dual specific antibodies, or antigen-binding fragments thereof, described herein which bind both IL4 and IL5 (e.g., B1, E7, and E7 affinity-matured variants) or IL4 and IL13 (e.g., F1 and F2) can be used to treat, suppress, or prevent disease, such as allergic, inflammatory, and autoimmune diseases (e.g., asthma); IL4-mediated disease; IL5-mediated disease; IL13-mediated disease; IL4/IL5-mediated disease; IL4/IL13-mediated disease; and/or proliferative disorders (e.g., cancer).

Examples of inflammatory and autoimmune diseases or disorders that may be treated by the dual specific antibodies, or antigen-binding fragments thereof, are described above. In some embodiments, the disease or disorder includes, but is not limited to, asthma such as asthma bronchiale, bronchial asthma, and auto-immune asthma.

Asthma is described as a chronic pulmonary disease that involves airway inflammation, hyperresponsiveness and obstruction. Physiologically, airway hyperresponsiveness is documented by decreased bronchial airflow after bronchoprovocation with methacholine or histamine. Other triggers that provoke airway obstruction include cold air, exercise, viral upper respiratory infection, cigarette smoke, and respiratory allergens. Bronchial provocation with allergen induces a prompt early phase immunoglobulin E (IgE)-mediated decrease in bronchial airflow followed in many patients by a late-phase IgE-mediated reaction with a decrease in bronchial airflow for 4-8 hours. The early response is caused by acute release of inflammatory substances, such as histamine, $PGD_2$, leukotriene, tryptase and platelet activating factor (PAF), whereas the late response is caused by de novo synthesized pro-inflammatory cytokines (e.g. TNFα, IL4, IL13) and chemokines (e.g. MCP-1 and MIP-1α) (Busse et al. In: Allergy: Principles and Practice, Ed. Middleston, 1173 (1998)). In chronic asthmatic patients, persistent pulmonary symptoms are mediated by the heightened response of Th2 cells. Th2 cytokines are believed to play a vital role in the disease (Larche et al., J. Allergy Clin. Immunol., 111: 450 (2003)), in particular, IL13 and IL4 produced by Th2 cells with NK phenotype (NKT) in the airway as indicated in a model of asthma in rodents (Akbari et al., Nature Med., 9: 582 (2003)). The gross pathology of asthmatic airways displays lung hyperinflation, smooth muscle hypertrophy, lamina reticularis thickening, mucosal edema, epithelial cell sloughing, cilia cell disruption, and mucus gland hypersecretion. Microscopically, asthma is characterized by the presence of increased numbers of eosinophils, neutrophils, lymphocytes, and plasma cells in the bronchial tissues, bronchial secretions, and mucus. Initially, there is recruitment of leukocytes from the bloodstream to the airway by activated CD4+ T-lymphocytes. The activated T-lymphocytes also direct the release of inflammatory mediators from eosinophils, mast cells, and lymphocytes. In addition, the Th2 cells produce IL4, IL5, IL9 and IL13. IL4, in conjunction with IL13, signals the switch from IgM to IgE antibodies.

Cross-linking of membrane-bound IgE molecules by allergen causes mast cells to degranulate, releasing histamine, leukotrienes, and other mediators that perpetuate the airway inflammation. IL5 activates the recruitment and activation of eosinophils. The activated mast cells and eosinophils also generate their cytokines that help to perpetuate the inflammation. These repeated cycles of inflammation in the lungs with injury to the pulmonary tissues followed by repair may produce long-term structural changes ("remodeling") of the airways.

Moderate asthma is currently treated with a daily inhaled anti-inflammatory-corticosteroid or mast cell inhibitor such as cromolyn sodium or nedocromil plus an inhaled beta2-agonist as needed (3-4 times per day) to relieve breakthrough symptoms or allergen- or exercise-induced asthma. Cromolyn sodium and nedocromil block bronchospasm and inflammation, but are usually effective only for asthma that is associated with allergens or exercise and typically, only for juvenile asthmatics. Inhaled corticosteroids improve inflammation, airways hyperreactivity, and obstruction, and reduce the number of acute exacerbations. However, it takes at least a month before effects are apparent and up to a year for marked improvement to occur. The most frequent side effects are hoarseness and oral fungal infection, i.e., candidiasis. More serious side effects have been reported, e.g., partial adrenal suppression, growth inhibition, and reduced bone formation, but only with the use of higher doses. Beclomethasone, triamcinolone, and flunisolide probably have a similar potency; whereas budesonide and fluticasone are more potent and reportedly have fewer systemic side effects.

Even patients with mild disease show airway inflammation, including infiltration of the mucosa and epithelium with activated T cells, mast cells, and eosinophils. T cells and mast cells release cytokines that promote eosinophil growth and maturation and the production of IgE antibodies, and these, in turn, increase microvascular permeability, disrupt the epithelium, and stimulate neural reflexes and mucus-secreting glands. The result is airways hyperreactivity, bronchoconstriction, and hypersecretion, manifested by wheezing, coughing, and dyspnea.

Traditionally, asthma has been treated with oral and inhaled bronchodilators. These agents help the symptoms of asthma, but do nothing for the underlying inflammation. Recognition during the last 10 years of the importance of inflammation in the etiology of asthma has led to the increased use of corticosteroids, but many patients continue to suffer from uncontrolled asthma.

The dual specific antibodies, or antigen-binding fragments thereof, with specificity for IL4, IL5, and/or IL13 would target multiple pathogenic pathways and can be used as a therapeutic, either alone or in combination with additional therapies (e.g., those known in the art or described above), for the treatment of asthma.

In additional embodiments, dual specific antibodies, or antigen-binding fragments thereof, may be used to treat cancer. The term cancer embraces a collection of proliferative disorders, including but not limited to pre-cancerous growths, benign tumors, and malignant tumors. Benign tumors remain localized at the site of origin and do not have the capacity to infiltrate, invade, or metastasize to distant sites. Malignant tumors will invade and damage other tissues around them. They can also gain the ability to break off from where they started and spread to other parts of the body (metastasize), usually through the bloodstream or through the lymphatic system where the lymph nodes are located. Primary tumors are classified by the type of tissue from which they arise; metastatic tumors are classified by the tissue type from which the cancer cells are derived. Over time, the cells of a malignant tumor become more abnormal and appear less like normal cells. This change in the appearance of cancer cells is called the tumor grade and cancer cells are described as being well-differentiated, moderately-differentiated, poorly-differentiated, or undifferentiated. Well-differentiated cells are quite normal appearing and resemble the normal cells from which they originated. Undifferentiated cells are cells that have become so abnormal that it is no longer possible to determine the origin of the cells.

IV. Dosages and Formulations

The antibody or antibody fragment compositions will be formulated, dosed, and administered in a fashion consistent with good medical practice. Factors for consideration in this context include the particular disorder being treated, the particular mammal being treated, the clinical condition of the individual patient, the cause of the disorder, the site of delivery of the agent, the method of administration, the scheduling of administration, and other factors known to medical practitioners. The "therapeutically effective amount" of the antibody or antibody fragment to be administered will be governed by such considerations, and is the minimum amount necessary to prevent, ameliorate, or treat an allergic, inflammatory, autoimmune, or proliferative disease or disorder, or symptoms thereof. The dosage and the timing of administering the antibody or antibody fragment of the invention will depend on various clinical factors including the overall health of the subject and the severity of the symptoms of, for example, the allergic disorder. The invention includes the use of antibodies or antibody fragments to treat, prevent, or reduce allergic disorders or symptoms therefrom, or the risk of developing allergic disorders in a subject. The antibody or antibody fragment can be administered at anytime, for example, after diagnosis or detection of an allergic disorder or a condition associated with an allergic disorder, or for prevention of an allergic disorder in subjects that have not yet been diagnosed with an allergic disorder but are at risk of developing such a disorder (e.g., subjects suffering from or being treated for a compromised immune system), after a risk of developing an allergic disorder is determined.

The dual specific antibodies, or antigen-binding fragments thereof, of the present invention can be formulated and administered in a variety of ways, e.g., those routes known for specific indications, including, but not limited to, inhalation, topically, orally, subcutaneously, bronchial injection, intravenously, intracerebrally, intranasally, transdermally, intraperitoneally, intramuscularly, intrapulmonary, vaginally, rectally, intraarterially, intracerebrospinally, intraarticularly, intrasynovially, intralesionally, parenterally, intraventricularly in the brain, or intraocularly. For example, the antibodies, or antibody fragments, can be in the form of a pill, tablet, capsule, liquid, or sustained release tablet for oral administration; or a liquid for intravenous, subcutaneous or administration; a polymer or other sustained release vehicle for local administration; an ointment, cream, gel, liquid, or patch for topical administration.

Local administration may be particularly desired if extensive side effects or toxicity is associated with IL4, IL5, or IL13 antagonism. An ex vivo strategy can also be used for therapeutic applications. Ex vivo strategies involve transfecting or transducing cells obtained from the subject with a polynucleotide encoding a dual specific antibody, or antigen-binding fragment thereof. The transfected or transduced cells are then returned to the subject. The cells can be any of a wide range of types including, without limitation, hemopoietic cells (e.g., bone marrow cells, macrophages, monocytes, dendritic cells, T cells, or B cells), fibroblasts, epithelial cells, endothelial cells, keratinocytes, or muscle cells.

For example, continuous systemic infusion or periodic injection of the dual specific antibodies, or antigen-binding fragments thereof, can be used to treat or prevent the disorder. Treatment can be continued for a period of time ranging from 1 day through the lifetime of the subject, more preferably 1 to 100 days, and most preferably 1 to 20 days and most preferably, until the symptoms of the allergic, inflammatory, autoimmune, or proliferative disease or disorder, or symptoms thereof are reduced or removed. Dosages vary depending on the compound and the severity of the condition. The dual specific antibodies, or antigen-binding fragments thereof, can be administered continuously by infusion, using a constant- or programmable-flow implantable pump, or by periodic injections. Sustained release systems can also be used. Semipermeable, implantable membrane devices are also useful as a means for delivering dual specific antibodies, or antigen-binding fragments thereof, in certain circumstances. In another embodiment, the dual specific antibodies, or antigen-binding fragments thereof, are administered locally, e.g., by inhalation, and can be repeated periodically. Pulmonary administration can also be employed, e.g., by use of an inhaler or nebulizer, and formulation with an aerosolizing agent. The antibody may also be administered into the lungs of a patient in the form of a dry powder composition (See e.g., U.S. Pat. No. 6,514,496).

The dosage of the dual specific antibodies, or antigen-binding fragments thereof, will depend on other clinical factors such as weight and condition of the subject and the route of administration of the compound. For treating subjects, between approximately 0.1 mg/kg to 500 mg/kg body weight of the dual specific antibodies, or antigen-binding fragments thereof, can be administered. A more preferable range is 1 mg/kg to 50 mg/kg body weight with the most preferable range being from 1 mg/kg to 25 mg/kg body weight. Depending upon the half-lives of the antibodies or antibody fragments in the particular subject, the antibodies or antibody fragments can be administered between several times per day to once a week. The methods of the present invention provide for single as well as multiple administrations, given either simultaneously or over an extended period of time.

Preferably, the dual specific antibodies, or antigen-binding fragments thereof, are administered parenterally or intravenously by continuous infusion or locally by inhaler. The dose and dosage regimen depends upon the severity of the disease, and the overall health of the subject. For parenteral administration, the dual specific antibodies, or antigen-binding fragments thereof, are formulated in a unit dosage injectable form (solution, suspension, emulsion) in association with a pharmaceutically acceptable parenteral vehicle. Such vehicles are inherently nontoxic, and non-therapeutic. Examples of such vehicles are water, saline, Ringer's solution, dextrose solution, and 5% human serum albumin. Nonaqueous vehicles such as fixed oils and ethyl oleate may also be used. Liposomes may be used as carriers. The vehicle may contain minor amounts of additives such as substances that enhance isotonicity and chemical stability, e.g., buffers and preservatives. The dual specific antibodies, or antigen-binding fragments thereof, typically are formulated in such vehicles at concentrations of about 1 mg/ml to 10 mg/ml. For administration by inhalation, the dual specific antibodies, or antigen-binding fragments thereof, are formulated in any suitable method to form the aerosol form of the present invention. A composition comprising the dual specific antibodies, or antigen-binding fragments thereof, is volatilized or nebulized with, or without, a pharmaceutically acceptable excipient to produce a vapor which can be condensed and breathed directly into the lungs using, for example, an inhaler. Pharmaceutically acceptable excipients can be volatile, and classes of such excipients are known in the art and include, without limitation, gaseous, supercritical fluid, liquid and solid solvents. Exemplary carriers within the classes include, without limitation, water, sterile saline, physiological buffer solutions like phosphate buffered saline, terpenes, alcohols, propylene glycol, glycerol and other similar alcohols, dry ice, dimethylformamide, dimethylacetamide, supercritical carbon dioxide, and mixtures thereof.

The dosage required depends on the choice of the route of administration; the nature of the formulation; the nature of the subject's illness; the subject's size, weight, surface area, age, and sex; other drugs being administered; and the judgment of the attending physician. Wide variations in the needed dosage are to be expected in view of the variety of polypeptides and fragments available and the differing efficiencies of various routes of administration. For example, oral administration would be expected to require higher dosages than administration by intravenous injection. Variations in these dosage levels can be adjusted using standard empirical routines for optimization as is well understood in the art. Administrations can be single or multiple (e.g., 2-, 3-, 6-, 8-, 10-, 20-, 50-, 100-, 150-, or more). Encapsulation of the polypeptide in a suitable delivery vehicle (e.g., polymeric microparticles or implantable devices) may increase the efficiency of delivery, particularly for oral delivery.

In one embodiment for the treatment of asthma, the dual specific antibody, or antigen-binding fragment thereof, need not be, but is optionally formulated with or administered in combination (simultaneously or sequentially) with one or more agents currently used to prevent or treat asthma or a risk of developing asthma. The antibody, or antigen-binding fragment thereof, can be formulated with, for example, an IgE antagonist, bronchodilator drugs (e.g., a beta2-adrenoceptor agonists, xanthines, cholinoceptor antagonists), anti-inflammatory agents (e.g., disodium cromoglycate (DSCG), nedocromil sodium, antihistamines such as ketotifen, corticosteroids such as prednisolone), theophylline, salbutamol, beclomethasone dipropionate, or another therapeutic asthma agent known in the art. The effective amount of such other agents depends on the amount of dual specific antibody, or antigen-binding fragment thereof, present in the formulation, the type of disorder or treatment, and other factors discussed above.

Therapeutic formulations are prepared using standard methods known in the art by mixing the active ingredient having the desired degree of purity with optional physiologically acceptable carriers, excipients or stabilizers (Remington's Pharmaceutical Sciences ($20^{th}$ edition), ed. A. Gennaro, 2000, Lippincott, Williams & Wilkins, Philadelphia, PA). Acceptable carriers, include saline, or buffers such as phosphate, citrate and other organic acids; antioxidants including ascorbic acid; low molecular weight (less than about 10 residues) polypeptides; proteins, such as serum albumin, gelatin or immunoglobulins; hydrophilic polymers such as polyvinylpyrrolidone, amino acids such as glycine, glutamine, asparagines, arginine or lysine; monosaccharides, disaccharides, and other carbohydrates including glucose, mannose, or dextrins; chelating agents such as EDTA; sugar alcohols such as mannitol or sorbitol; salt-forming counterions such as sodium; and/or nonionic surfactants such as TWEEN™, PLURONICS™, or PEG.

Optionally, but preferably, the formulation contains a pharmaceutically acceptable salt, preferably sodium chloride, and preferably at about physiological concentrations. Optionally, the formulations of the invention can contain a pharmaceutically acceptable preservative. In some embodiments the preservative concentration ranges from 0.1 to 2.0%, typically v/v. Suitable preservatives include those known in the pharmaceutical arts. Benzyl alcohol, phenol, m-cresol, methylparaben, and propylparaben are exemplary preservatives. Optionally, the formulations of the invention can include a pharmaceutically acceptable surfactant at a concentration of 0.005 to 0.02%.

The formulation herein may also contain more than one active compound as necessary for the particular indication being treated, preferably those with complementary activities that do not adversely affect each other. Such molecules are suitably present in combination in amounts that are effective for the purpose intended.

The active ingredients may also be entrapped in microcapsule prepared, for example, by coacervation techniques or by interfacial polymerization, for example, hydroxymethylcellulose or gelatin-microcapsule and poly-(methylmethacylate) microcapsule, respectively, in colloidal drug delivery systems (for example, liposomes, albumin microspheres, microemulsions, nano-particles and nanocapsules) or in macroemulsions. Such techniques are disclosed in Remington's Pharmaceutical Sciences, supra.

Sustained-release preparations may be prepared. Suitable examples of sustained-release preparations include semipermeable matrices of solid hydrophobic polymers containing the antibody, which matrices are in the form of shaped articles, e.g., films, or microcapsule. Examples of sustained-release matrices include polyesters, hydrogels (for example, poly(2-hydroxyethyl-methacrylate), or poly(vinylalcohol)), polylactides (U.S. Pat. No. 3,773,919), copolymers of L-glutamic acid and γ ethyl-L-glutamate, non-degradable ethylene-vinyl acetate, degradable lactic acid-glycolic acid copolymers such as the LUPRON DEPOT™ (injectable microspheres composed of lactic acid-glycolic acid copolymer and leuprolide acetate), and poly-D-(–)-3-hydroxybutyric acid. While polymers such as ethylene-vinyl acetate and lactic acid-glycolic acid enable release of molecules for over 100 days, certain hydrogels release proteins for shorter time periods. When encapsulated antibodies remain in the body for a long time, they may denature or aggregate as a result of exposure to moisture at 37° C., resulting in a loss of biological activity and possible changes in immunogenicity. Rational strategies can be devised for stabilization depending on the mechanism involved. For example, if the aggregation mechanism is discovered to be intermolecular S—S bond formation through thio-disulfide interchange, stabilization may be achieved by modifying sulfhydryl residues, lyophilizing from acidic solutions, controlling moisture content, using appropriate additives, and developing specific polymer matrix compositions.

In one example, the dual specific antibody, or antigen-binding fragment thereof, is administered locally, e.g., by direct injections, when the disorder permits, and the injections can be repeated periodically, or by inhalation. The dual specific antibody, or antigen-binding fragment thereof, can also be delivered systemically to the subject or directly to the afflicted area.

The invention also provides a composition comprising the dual specific antibody, or antigen-binding fragment thereof, and a pharmaceutically acceptable carrier or diluent. This composition for therapeutic use is sterile and may be lyophilized. Also contemplated is the use of a dual specific antibody, or antigen-binding fragment thereof, of this invention in the manufacture of a medicament for treating an indication described herein. The composition can further comprise a second therapeutic agent such as an anti-asthma agent, an anti-inflammatory agent, or an anti-proliferative agent (e.g., a chemotherapeutic agent, a cytotoxic agent or an anti-angiogenic agent).

V. Articles of Manufacture and Kits

Another embodiment of the invention is an article of manufacture containing materials useful for the treatment of diseases or disorders (e.g., allergic diseases or disorders or asthma). Yet another embodiment of the invention is an article of manufacture containing materials useful for the treatment of inflammatory, autoimmune, and proliferative diseases or disorders. The article of manufacture comprises a container and a label or package insert on or associated with the container. Suitable containers include, for example, bottles, vials, syringes, etc. The containers may be formed from a variety of materials such as glass or plastic. The container holds a composition which is effective for treating the condition and may have a sterile access port (for example the container may be an intravenous solution bag or a vial having a stopper pierceable by a hypodermic injection needle). At least one active agent in the composition is a dual specific antibody or antigen-binding fragment of the invention. The label or package insert indicates that the composition is used for treating the particular condition. The label or package insert will further comprise instructions for administering the antibody composition to the patient. Articles of manufacture and kits comprising combinatorial therapies described herein are also contemplated.

Package insert refers to instructions customarily included in commercial packages of therapeutic products that contain information about the indications, usage, dosage, administration, contraindications and/or warnings concerning the use of such therapeutic products. In one embodiment, the package insert indicates that the composition is used for treating asthma.

Additionally, the article of manufacture may further comprise a second container comprising a pharmaceutically-acceptable buffer, such as bacteriostatic water for injection (BWFI), phosphate-buffered saline, Ringer's solution and dextrose solution. It may further include other materials desirable from a commercial and user standpoint, including other buffers, diluents, filters, needles, and syringes.

Kits are also provided that are useful for various purposes, e.g., for purification or immunoprecipitation of IL4, IL5, or IL13 from cells. For isolation and purification of IL4, IL5, or IL13, the kit can contain a IL4/IL5 or IL4/IL13 antibody coupled to beads (e.g., sepharose beads). Kits can be provided which contain the antibodies for detection and quantitation of IL4, IL5, or IL13 in vitro, e.g., in an ELISA or a Western blot. As with the article of manufacture, the kit comprises a container and a label or package insert on or associated with the container. The container holds a composition comprising at least one dual specific or multispecific antibody or antibody fragment of the invention. Additional containers may be included that contain, e.g., diluents and buffers or control antibodies. The label or package insert may provide a description of the composition as well as instructions for the intended in vitro or diagnostic use.

The following Examples are offered for illustrative purposes only, and are not intended to limit the scope of the present invention in any way. Indeed, various modifications of the invention in addition to those shown and described herein will become apparent to those skilled in the art from the foregoing description and fall within the scope of the appended claims.

EXAMPLES

Commercially available reagents referred to below in the Examples were used according to manufacturer's instructions unless otherwise indicated. The source of those cells identified in the following Examples, and throughout the specification, by ATCC accession numbers is the American Type Culture Collection, Manassas, VA. Unless otherwise noted, the present invention uses standard procedures of recombinant DNA technology, such as those described hereinabove and in the following textbooks: Sambrook et al., supra; Ausubel et al., *Current Protocols in Molecular Biology* (Green Publishing Associates and Wiley Interscience, N.Y., 1989); Innis et al., *PCR Protocols: A Guide to Methods and Applications* (Academic Press, Inc.: N.Y., 1990); Harlow et al., *Antibodies: A Laboratory Manual* (Cold Spring Harbor Press: Cold Spring Harbor, 1988); Gait, *Oligonucleotide Synthesis* (IRL Press: Oxford, 1984); Freshney, *Animal Cell Culture*, 1987; Coligan et al., *Current Protocols in Immunology*, 1991.

Example 1. Library Design and Construction

By mutation in the light chain (LC) complementarity determining regions (CDRs), a monospecific antibody can recruit a second binding specificity toward a new antigen while maintaining its primary antigen specificity. Further, the dual binding can be affinity-matured to $K_D$ of low nanomolar. This path of engineering dual specificity is well suited for antibodies that mainly utilize the heavy chain (HC) CDRs for binding their primary antigens. Here, we describe a mouse hybridoma-derived anti-interleukin 4 antibody, which heavily depends on LC CDRs for binding energy, and the evolution of this antibody to dual specificity with mutation in the HC CDRs alone or with further mutation in the LC CDRs. One such dual specific variant toward both interleukin 4 (IL4) and interleukin 5 (IL5) is matured to high dual affinity with $K_D$ of low nanomolar. The results further highlight the ability of the antibody to evolve dual specificity and demonstrate a generally applicable engineering path for evolving dual specificity in any antibody using a strategy of mutation scanning to identify regions of an antigen-binding site that may tolerate mutation and allow for evolution of secondary binding specificity.

We set out to recruit a second antigen specificity into a humanized antibody 19C11 (hu19C11, humanized in the backbone of germline VH1 and kappa I), which binds IL4 and blocks it from engaging IL4 receptor α. We first cloned its Fab into a "phagemid" construct (pV0115) to co-express the LC and, bicistronically, the variable domain and constant domain 1 ($C_H1$) of HC C-terminally fused to M13 minor coat protein p3 as described (Lee et al., J. Mol. Biol. 340:1073-93, 2004). A portion of the hinge region of IgG with amino acid sequence KTHTC was included between CH1 and M13 p3 to allow bivalent Fab display (Lee et al., J. Mol. Biol. 340:1073-93, 2004) to increase the efficiency of binding to antigens immobilized on a solid surface support. We first verified that the Fab-displaying phage bound well to an antibody against the expression tag (gD) C-terminally fused to LC and to IL4 with high affinity (phage $EC_{50}$=1 nM), which is similar to the measured affinity of the antibody as IgG.

Figure 1C:
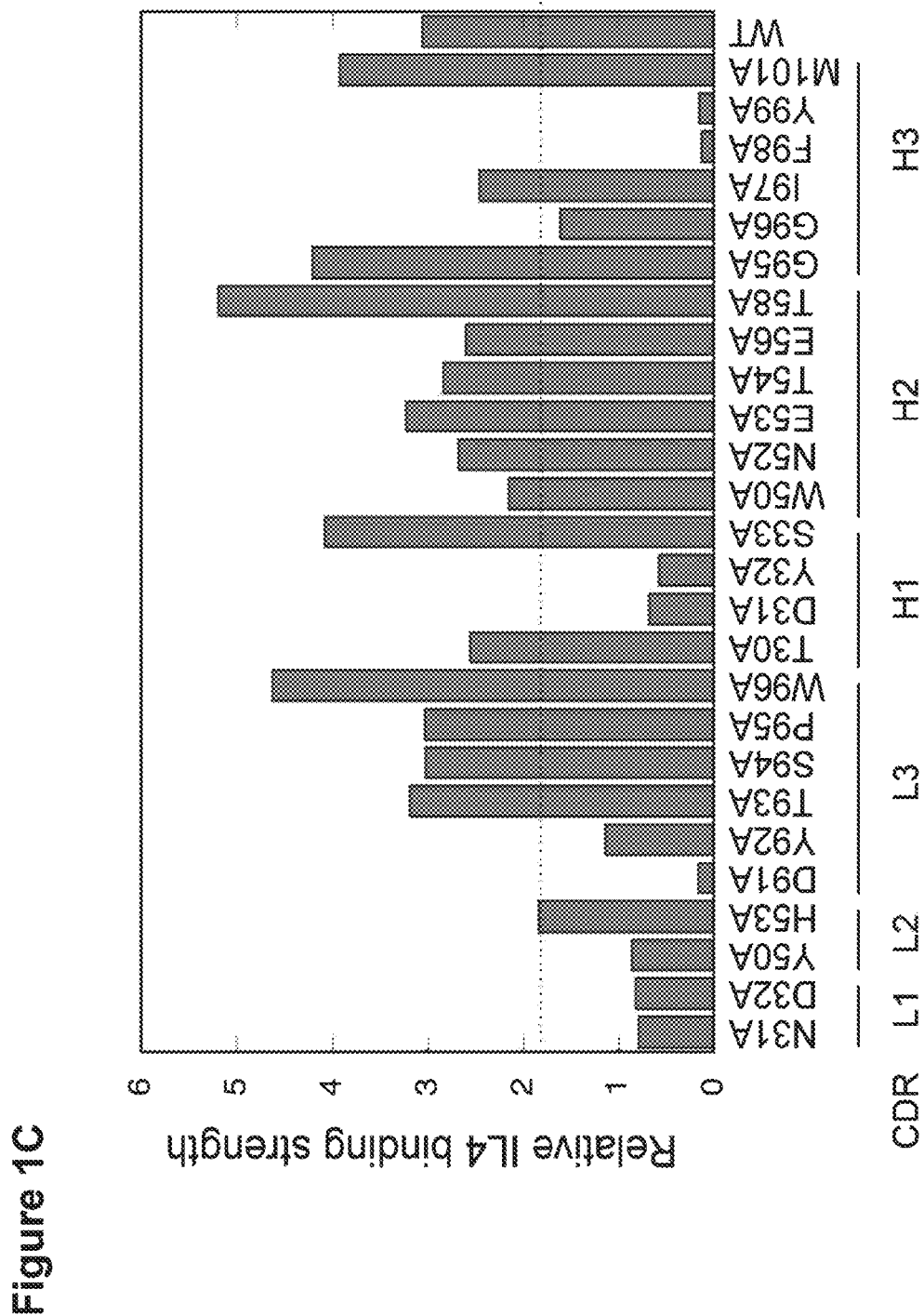
FIG. 1C is a graph showing the effects of alanine mutations at individual sites of CDRs were examined by comparing the relative IL4 binding affinity of phage displaying Fab variants by performing assays as in FIGS. 1A and 1B. Single letter codes of amino acids are used. Relative IL4-binding strengths were determined by fitting the data with a linear regression model and then dividing the slope of IL4 binding (versus phage concentration) by the slope of Fab expression. Low values (below the dotted line) were deemed low IL4 binding affinity relative to hu1911 wt indicating disruptive mutations.
Figure 2A:
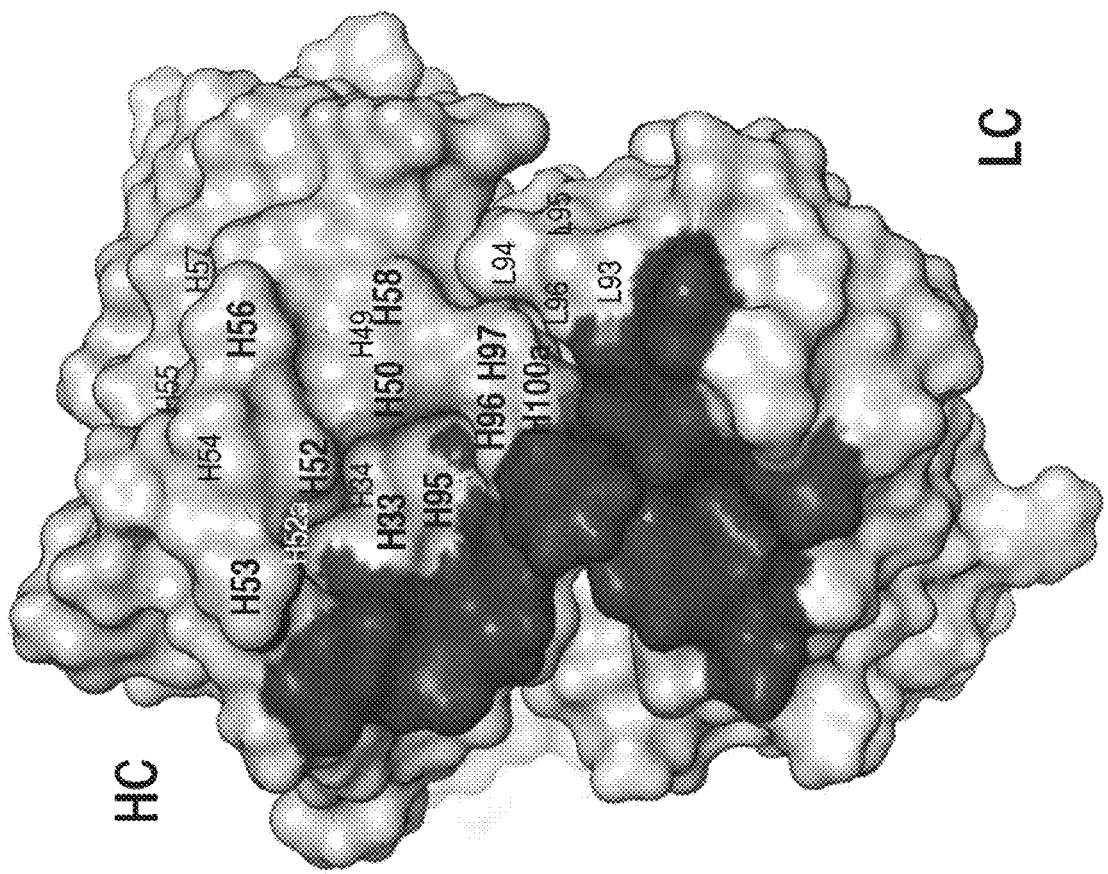
FIG. 2A is a structural diagram showing the critical residues of IL4 binding of hu19C11 mapped onto a top-down view of the structure of trastuzumab Fab (PDB: 1FDV). The structural model of hu19C11 was generated using MOE using the POB entries 3SQO and 3BEI as templates for the heavy and light chain, respectively. Residues important for IL4 binding are LC residues 31, 32, 50, 53, 91, 92, and HC residues 31, 32, 96, 98, and 99 (in Kabat numbering). The residues are colored in red on the model structure in a top down view of the antigen-binding site. Libraries of hu19C11 Fab variants displayed on phage were generated by site directed mutation. HC residues that were allowed all 20 amino acids with preference for wild-type residues are labeled in bold while other HC and LC residues as labeled were allowed lim For example, allergic, inflammatory, or autoimmune disorders (e.g., asthma) often involve multiple cytokines. Dual specific antibodies are useful in both therapeutic and diagnostic applications where the targeting of more than one antigen is desired. We have discovered a novel method for generating dual specific antibodies. When the antibody $V_L$ includes residues that are critical for antibody-antigen interaction, such antibodies can then be diversified by alteration of the $V_H$ residues alone or in combination with additional $V_L$ and framework residues.
Figure 3:
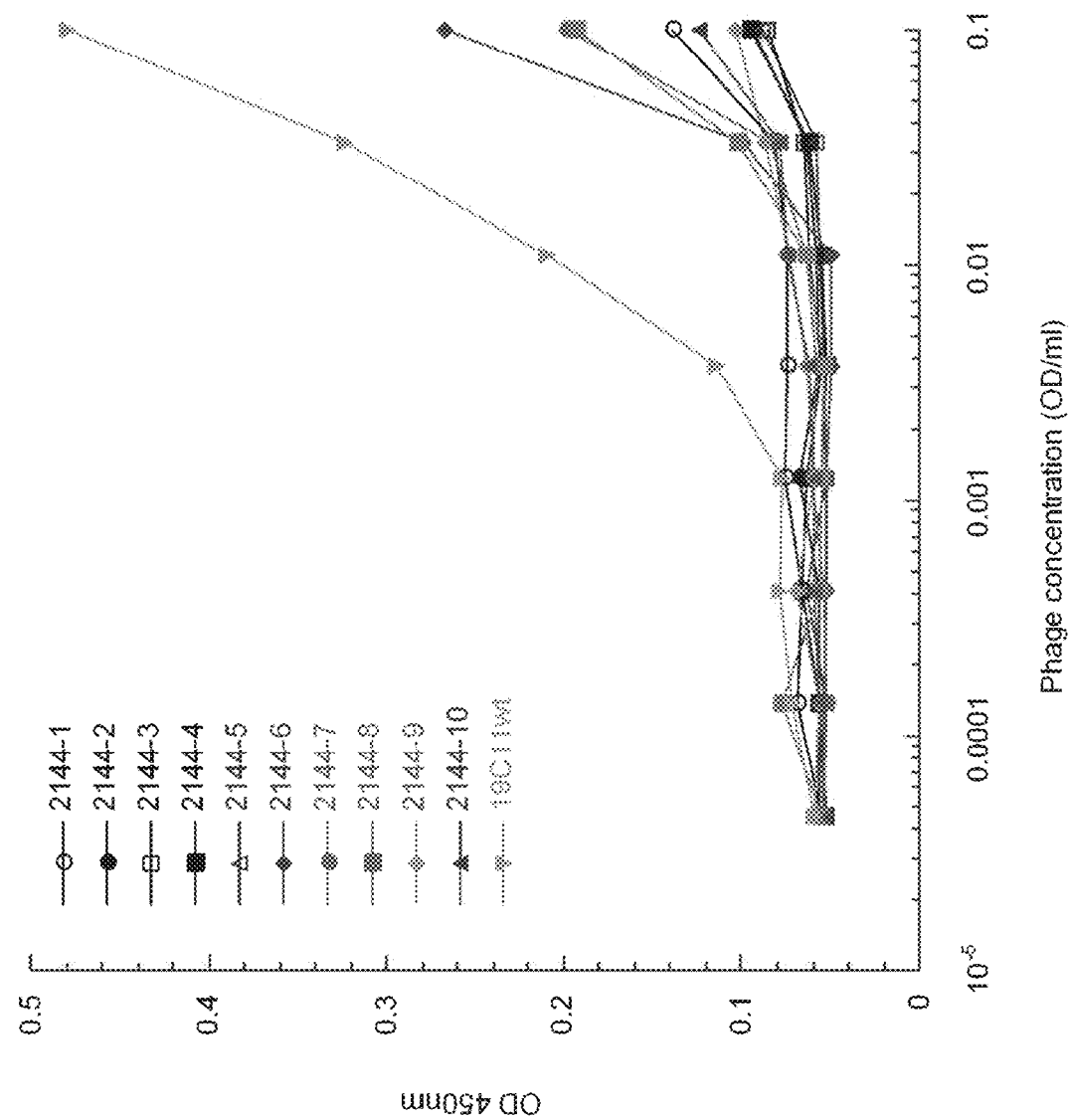
Figure 5:
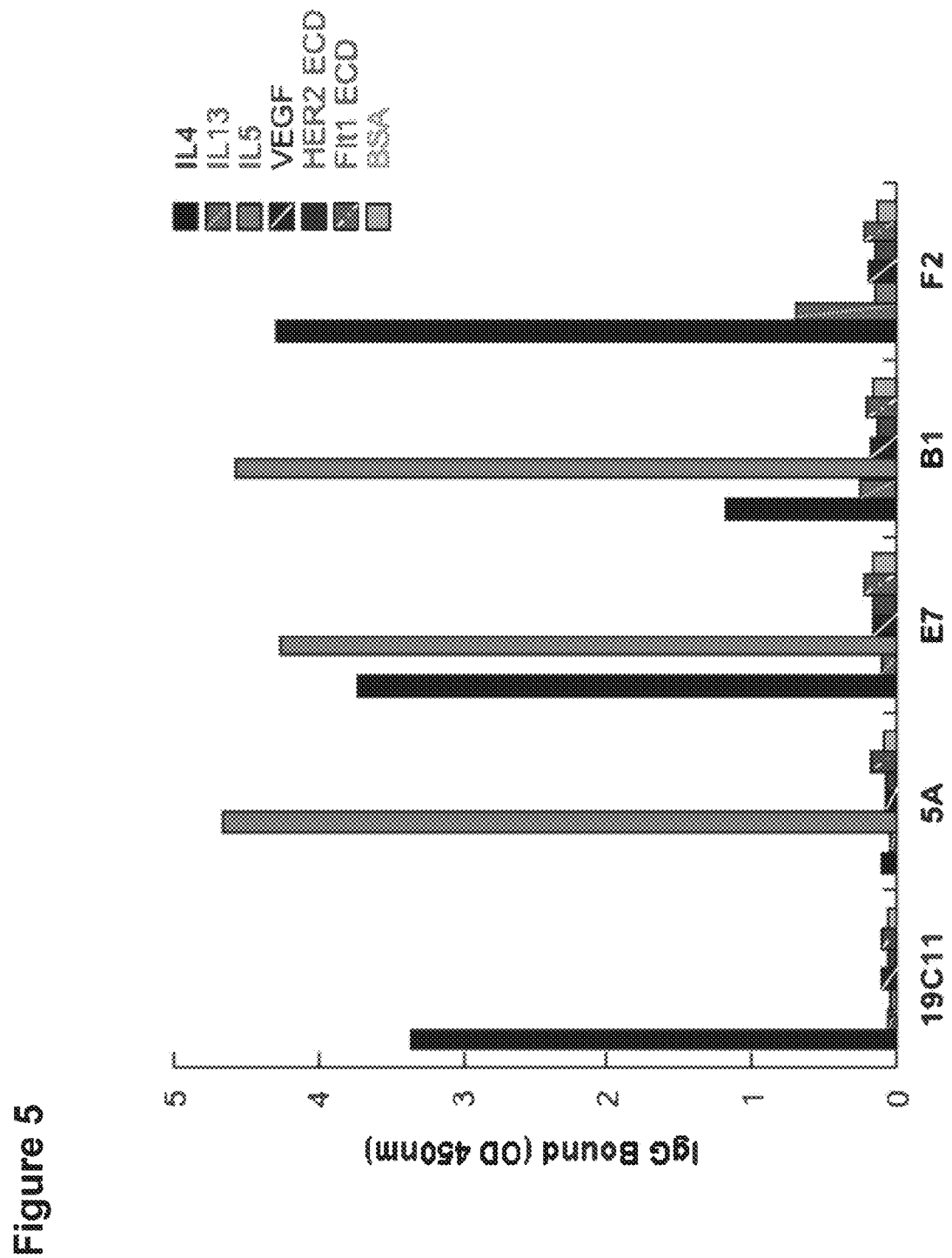
Figure 6:
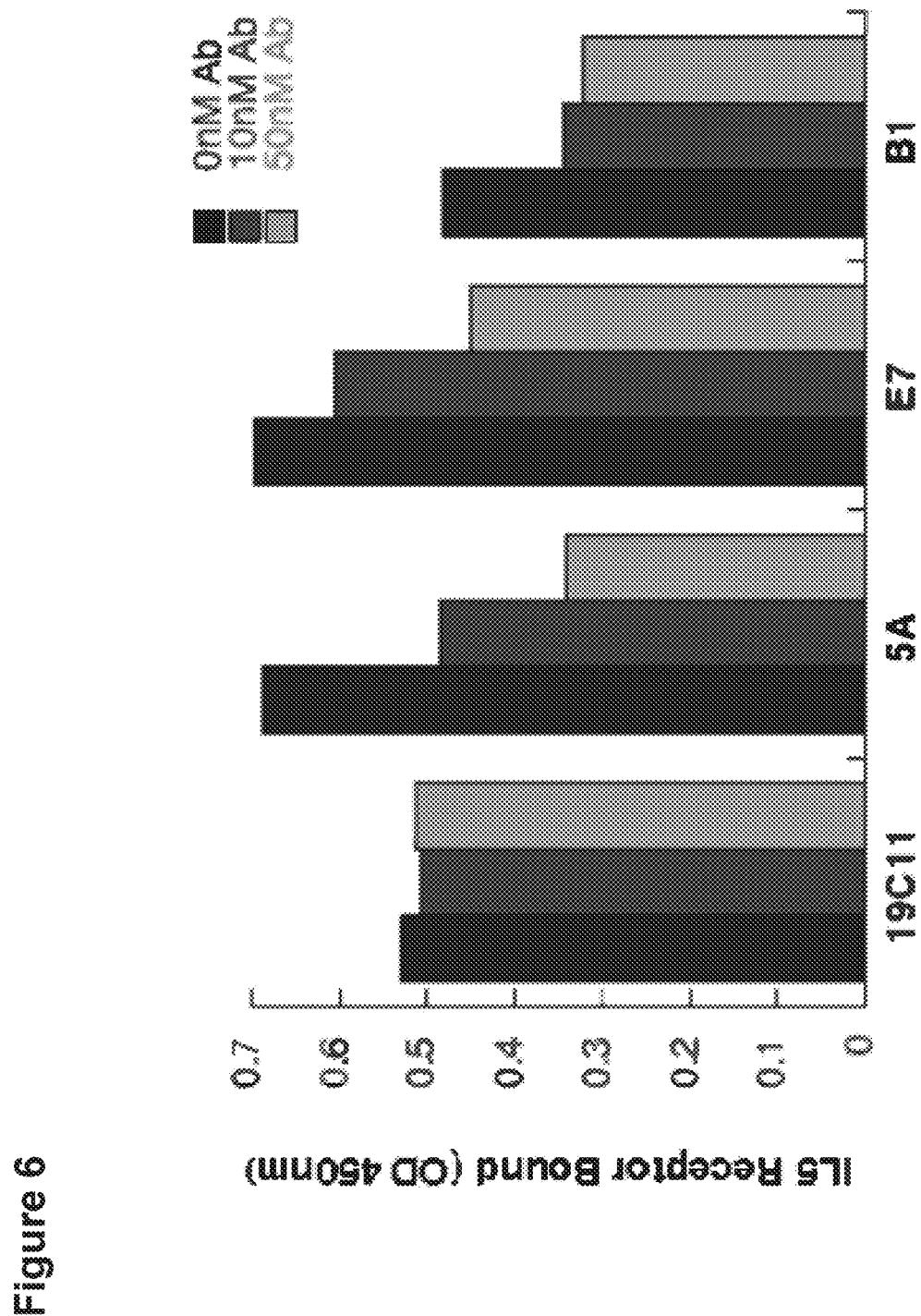

To determine the engineering strategy of recruiting a secondary binding specificity to hu19C11, we first examined the importance of its three LC CDRs for binding IL4 by mutating two or three residues of each LC CDR to alanine. These LC CDR positions were selected since they were identified previously as key positions for combinatorial mutagenesis in the LC library approach for selecting dual specific clones from antibodies relying heavily on HC CDRs for their primary antigen binding (Bostrom et al. *PLoS One.* 6:e17887, 2011). Phage displaying hu19C11 wild-type, alanine mutants L1 (I30A/N31A/D32A), L2 (Y50A/H53A/R54A), or L3 (D91A/Y92A) were immobilized to anti-gD antibody (FIG. 1A) or IL4 (FIG. 1B) and assayed using ELISA for binding. We found that LC CDRs appeared energetically important. Phage displaying Fab with alanine mutations in any of three LC CDRs exhibited no detectable binding to IL4 but bound to the anti-gD antibody, indicating that these mutants were indeed displayed on phage, albeit with lower level than the wild type Fab but their binding to IL4 was severely disrupted (FIGS. 1A and 1B). Therefore, the approach of generating randomized LC CDR libraries will not likely produce dual specific antibodies since the number of amino acid residues available for evolving secondary antigen binding is quite limited. We next mutated individual key residues of LC CDRs as well as surface accessible HC CDRs as previously described (Sidhu et al. *J Mol Biol.* 338:299-310, 2004; Lee et al. *J Mol Biol.* 340:1073-1093, 2004) and evaluated their role in IL4 binding by determining the relative binding affinity of these alanine mutants compared to wild type hu19C11. The results verified the importance of those key LC CDR residues for IL4 binding. However, all tested positions of CDR H2 and half of the CDR H1 and H3 appeared tolerant to mutation (FIG. 1C).

Figures 8A, 8B:
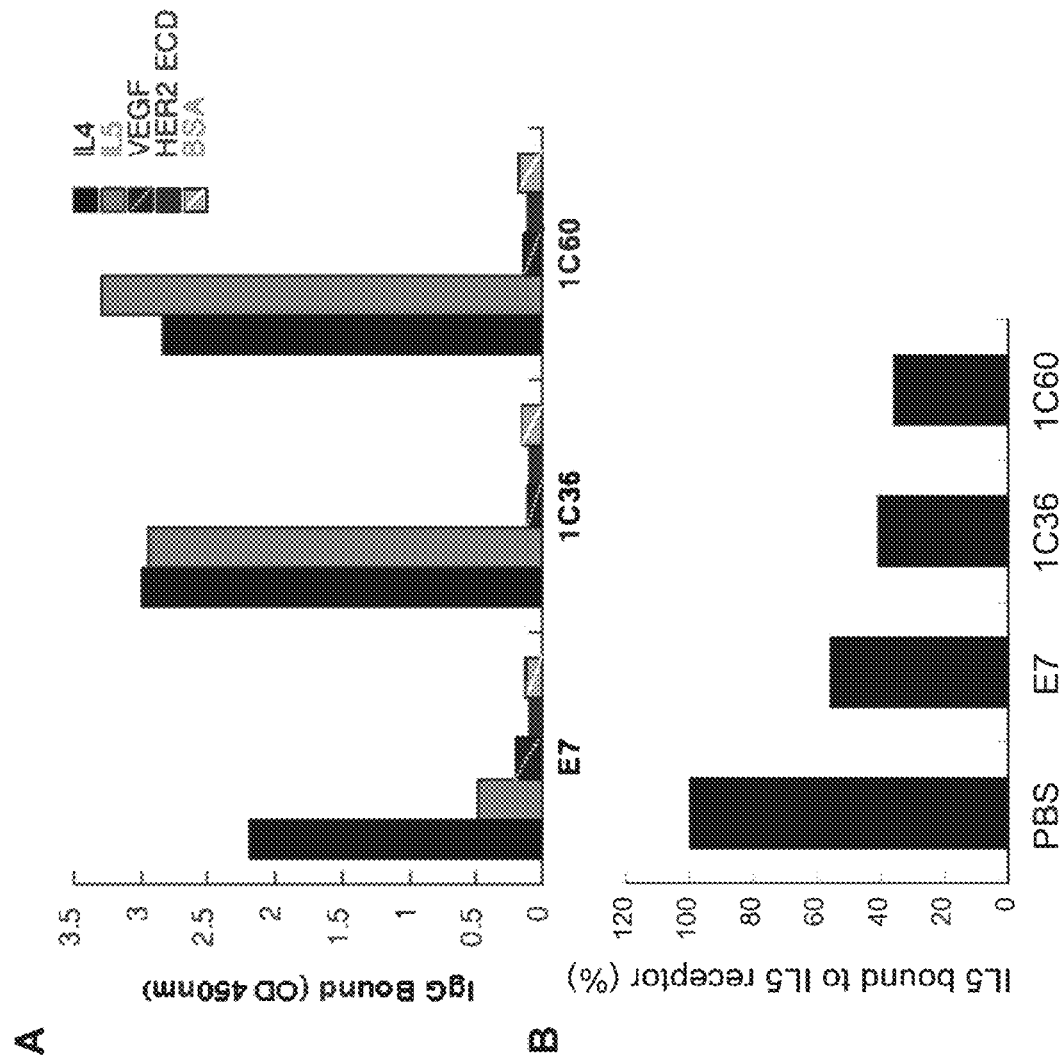

By mapping the residues that are critically important for IL4 binding (LC residues 30, 31, 32, 50, 53, 54, 91, 92; HC residues 31, 32, 98, 99 (in Kabat numbering)) on the structure of Trastuzumab Fab (PDB: 1 FDV) as a model, we identified an area centered at CDR H2 that tolerated mutation and may be suitable to evolve a second specificity (FIG. 2A). We then selected a set of residues in CDR H1 (33, 34), H2 (50-58), H3 (95-97), and L3 (93-96) that tolerated alanine mutation for randomization centering on CDR H2 for the mutation scheme, and used one set of synthetic oligonucleotides directed to randomize these selected residues at each of the four CDRs according to the mutagenesis method of Kunkel et al. (Kunkel et al., *Methods Enzymol.* 154:367-82, 1987). The randomization scheme was guided by diversity in natural antibodies in terms of amino acid composition and the length variability of CDR H2 and CDR L3 (FIG. 2B). The template for mutagenesis contained a stop codon only in the CDR H2, which ensured mutation in this CDR in the Fab-displaying libraries. We generated ten phage-display libraries, each with sizes ranging from $10^8$-$10^9$. As assessed by phage titrations of hu19C11 and the ten HC libraries (2144-1 through 2144-10) binding to immobilized IL4 (PeproTech) captured by a non-blocking anti-IL4 antibody, each library, as a pool, showed some low level of binding toward IL4 that was generally much reduced compared to the template antibody hu19C11, indicating different levels of disruption of IL4 binding on average (FIG. 3).

We chose IL5 and IL13 as the secondary antigens. While these two interleukins, like IL4, belong to the 4-helix bundle cytokine family, they are quite divergent at the level of amino acid sequence and structural organization (LaPorte et al. *Cell.* 132:259-272, 2008; Patino et al. *Structure.* 19:1864-1875, 2011; Finkelman et al. *J Immunol.* 184:1663-1674, 2010). The sequence identity between IL4 and IL13 is 12%, whereas that of IL4 and IL5 is 11%. Structurally, IL5 forms a unique intertwined homo-dimer with one α-helix from one chain forming a 4-helix bundle with three α-helixes from the other chain (Milburn et al. *Nature.* 363:172-176, 1993; Patino et al. *Structure.* 19:1864-1875, 2011); IL4 and IL13 are both monomers. However, the three cytokines are related in their biological function and dual specific antibodies that bind and block two of these cytokines may have potential utility as treatments for allergic diseases such as asthma 9 (Finkelman et al. *J Immunol.* 184:1663-1674, 2010; Haldar et al. *N Engl J Med.* 360:973-984, 2009).

We performed several rounds of panning and enrichment for IL5 or IL13 binding clones that retained IL4 binding from the constructed phage display libraries as previously described (Bostrom et al. *Science.* 323:1610-1614, 2009). By screening approximately 100 clones each, we found 3 to 8 clones that exhibited dual binding to IL5/IL4 or IL13/IL4, respectively. And from sequencing, two unique IL4/IL5 binding clones (B1, E7) and two unique IL4/IL13 (FI, F2) binding clones were identified (FIG. 2B). We also isolated clones that bound solely to IL5 (e.g., clone 5A). With the exception of clone B1, all clones contained mutations only in HC CDRs compared to their mono-specific parent template (FIGS. 4A-4C). This demonstrated that mutation of HC CDRs of a monospecific antibody can confer dual specificity. We used phage binding competition assays to estimate clone affinity as the concentration of interleukins needed to inhibit 50% of Fab displaying phage from binding to immobilized interleukins ($IC_{50}$). We found that binding to the secondary antigens was weak with $IC_{50}$ in the micro molar range while IL4 binding was maintained in the low nanomolar range.

Example 2. Evaluation of Library Performance

To verify the dual binding specificity, the clones B1, E7, F2, and 5A were expressed as IgGs, and binding of the resultant IgGs to the expected antigens but not to several other proteins was confirmed (FIG. 5). We further tested binding specificity by demonstrating minimal binding of IgGs to the human epithelial kidney cell line 293 cells by flow cytometry, which do not express IL4, IL5, and IL13, as well as to baculovirus (BV) particles generated from insect cell lines by ELISA (Hotzel et al. *MAbs.* 4:753-760, 2012). Furthermore, the IL4/IL5 dual specific antibodies B1 and E7 along with the monospecific IL5 binding antibody were shown to block IL5 from binding the IL5 receptor α, suggesting that the binding epitopes on IL5 overlapped with that of IL5 receptor (FIG. 6). By surface plasmon resonance (SPR) measurements, the IL4/IL5 dual specific clone E7 had low affinity toward IL5 ($K_D$=905 nM) but maintaining the high affinity IL4 binding ($K_D$=3.4 nM) of its parent antibody hu19C11, as measured by surface plasmon resonance (SPR) (FIGS. 7A and 7B).

Example 3. Affinity Maturation of Dual Specific Antigen-Binding Fragment

To improve the dual affinity of E7, we randomized E7 CDRs through site-directed mutagenesis and displayed the variants on phage for binding selection. Three libraries were generated targeting residues of CDR H2 and CDR L3 (H2/L3 library), residues of CDR H1, H2 and H3 (H1/H2/H3 library), or residues of CDR H2 and selected sites in framework region 3 (FR3) of HC (H2/FR3 library) for randomization as described (Lee et al. *J Mol Biol.* 340:1073-

1093, 2004; Bostrom et al. *Methods Mol Biol.* 525:1-24, 2009; Lee et al. *Blood.* 108:3103-3111, 2006) (FIG. 7A). As clone E7 maintained high IL4 binding affinity, we focused the library selection on improving IL5 binding. From the H1/H2/H3 library, we found many clones with improved affinity toward IL5 but with greatly reduced affinity toward IL4, whereas clones from the H2/L3 library and the H2/FR3 library showed improved IL5 binding without loss of IL4-binding affinity (FIG. 4A). Select clones were purified as IgGs and compared to E7. Many variants from the H2/L3 library exhibited higher dual binding as IgG without increasing binding to a set of non-targeted proteins (FIG. 8A). We also confirmed the low off target binding using BV binding and 293 cell FACS as above and that the improved clones still blocked IL5 from binding to its receptor (FIG. 8B). Monovalent binding affinities of the two improved variants, 1C36 and 1C60 (FIGS. 7C and 7D), were determined by SPR measurements as Fabs binding to immobilized IL4 or IL5. Both variants maintained high affinity toward IL4 ($K_D$=3-4 nM) and improved affinity toward IL5 by 37-fold and 20-fold respectively ($K_D$=24.1 nM for 1C36 and 44.4 nM for 1060) (FIG. 7B).

In summary, we showed that mutation in the HC CDRs of a monospecific antibody may recruit a secondary binding specificity, and we improved one of the isolated dual specific antibodies to low nM affinity toward both antigens. Previously, we demonstrated that Trastuzumab Fab evolves dual specificity through mutation in the LC CDRs; other dual specific antibodies have since been generated using the same LC approach. Together with the findings of the current study, we highlighted the evolvability of the binding specificity of antibodies. We found that with limited mutation in the CDRs on the side of not just light chain but also heavy chain, an antibody may add on another binding specificity. In nature, antibodies are constantly under remodeling by gene shuffling and somatic mutation. It has been shown that antibodies can be "reused" by turning into antibodies with different binding properties, hence different function through somatic mutation. Antibodies may have one of the ideal folds and structures for evolving binding specificity by limited mutation, which should play a role in the vast capacity of the natural immune response to recognize essentially infinite varieties of foreign antigens. Further, this work shows, for the first time, a general engineering path to evolve a dual specific antibody from any monospecific antibody summarized as follows. Through mutagenesis analysis (e.g., alanine scanning) one can first identify the region of antigen binding site that tolerates mutation without severely disrupting the binding of its primary antigen.

OTHER EMBODIMENTS

All patents, patent applications, patent application publications, and other publications cited or referred to in this specification are herein incorporated by reference to the same extent as if each independent patent, patent application, patent application publication or publication was specifically and individually indicated to be incorporated by reference.

What is claimed is:

1. An isolated dual specific antibody, or antigen-binding fragment thereof, capable of binding interleukin 4 (IL4) and interleukin 5 (IL5), comprising the following six CDRs:
   (i) a CDRL1 comprising the amino acid sequence of KASQSVINDAA (SEQ ID NO: 9);
   (ii) a CDRL2 comprising the amino acid sequence of YTSHRYT (SEQ ID NO: 10);
   (iii) a CDRL3 comprising the amino acid sequence of QQDYKHPWTF (SEQ ID NO: 31);
   (iv) a CDRH1 comprising the amino acid sequence of DYFIH (SEQ ID NO: 15);
   (v) a CDRH2 comprising the amino acid sequence of AGIVYDATGFTVYADDFK (SEQ ID NO: 32); and
   (vi) a CDRH3 comprising the amino acid sequence of GGIFYGMDY (SEQ ID NO: 20).

2. The isolated dual specific antibody, or antigen-binding fragment thereof, of claim 1, further comprising a framework region 3 (FR3) comprising the amino acid sequence of $GRX_1TITX_2DX_3STSTX_4$ (SEQ ID NO: 26), wherein $X_1$ is Val or Phe, $X_2$ is Arg or Ile, $X_3$ is Thr, Phe, Met, or Pro, and $X_4$ is Ala or Val.

3. The isolated dual specific antibody, or antigen-binding fragment thereof, of claim 1, wherein said antibody binds IL4 with a Kd of 10 nM or lower and IL5 with a Kd of about 50 nM or lower.

4. The isolated dual specific antibody, or antigen-binding fragment thereof, of claim 1, wherein said antibody is an IgG antibody.

5. The isolated dual specific antibody, or antigen-binding fragment thereof, of claim 1, wherein said fragment is a Fab fragment or a single chain variable fragment (scFv).

6. The isolated dual specific antibody, or antigen-binding fragment thereof, of claim 1, wherein at least a portion of the framework sequence is a human consensus framework sequence.

7. The isolated dual specific antibody, or antigen-binding fragment thereof, of claim 1, wherein the antibody is a chimeric antibody.

8. The isolated dual specific antibody, or antigen-binding fragment thereof, of claim 1, wherein the antibody is a humanized antibody.

9. A pharmaceutical composition comprising the isolated dual specific antibody, or antigen-binding fragment thereof, of claim 1, and a pharmaceutically acceptable excipient.

10. An isolated dual specific antibody, or antigen-binding fragment thereof, capable of binding IL4 and IL5, comprising a light chain variable region comprising the amino acid sequence of SEQ ID NO: 33 and a heavy chain variable region comprising the amino acid sequence of SEQ ID NO: 34.

11. A pharmaceutical composition comprising the isolated dual specific antibody, or antigen-binding fragment thereof, of claim 10, and a pharmaceutically acceptable excipient.

* * * * *

UNITED STATES PATENT AND TRADEMARK OFFICE
CERTIFICATE OF CORRECTION

| | | |
|---|---|---|
| PATENT NO. | : 12,006,360 B2 | Page 1 of 1 |
| APPLICATION NO. | : 16/860891 | |
| DATED | : June 11, 2024 | |
| INVENTOR(S) | : Fuh et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 736 days.

Signed and Sealed this
Thirty-first Day of December, 2024

Derrick Brent
*Acting Director of the United States Patent and Trademark Office*

SEQUENCE LISTING

```
<160> NUMBER OF SEQ ID NOS: 34

<210> SEQ ID NO 1
<211> LENGTH: 107
<212> TYPE: PRT
<213> ORGANISM: Artificial Sequence
<220> FEATURE:
<223> OTHER INFORMATION: Synthetic Construct

<400> SEQUENCE: 1

Asp Ile Gln Met Thr Gln Ser Pro Ser Ser Leu Ser Ala Ser Val Gly
1               5                   10                  15

Asp Arg Val Thr Ile Thr Cys Lys Ala Ser Gln Ser Val Ile Asn Asp
                20                  25                  30

Ala Ala Trp Tyr Gln Gln Lys Pro Gly Lys Ala Pro Lys Leu Leu Ile
            35                  40                  45

Tyr Tyr Thr Ser His Arg Tyr Thr Gly Val Pro Ser Arg Phe Ser Gly
    50                  55                  60

Ser Gly Ser Gly Thr Asp Phe Thr Leu Thr Ile Ser Ser Leu Gln Glu
65                  70                  75                  80

Asp Phe Ala Thr Tyr Tyr Cys Gln Gln Asp Tyr Thr Ser Pro Trp Thr
                85                  90                  95

Phe Gly Gln Gly Thr Lys Val Glu Ile Lys Arg
            100                 105

<210> SEQ ID NO 2
<211> LENGTH: 118
<212> TYPE: PRT
<213> ORGANISM: Artificial Sequence
<220> FEATURE:
<223> OTHER INFORMATION: Synthetic Construct
```

-continued

```
<400> SEQUENCE: 2

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asp Tyr
            20                  25                  30

Ser Met His Trp Val Arg Gln Ala Pro Gly Gln Gly Leu Glu Trp Ile
        35                  40                  45

Val Trp Ile Asn Thr Glu Thr Gly Glu Pro Thr Tyr Ala Asp Asp Phe
    50                  55                  60

Lys Gly Arg Val Thr Ile Thr Arg Asp Thr Ser Thr Ser Thr Ala Tyr
65                  70                  75                  80

Leu Glu Leu Ser Ser Leu Arg Ser Glu Asp Thr Ala Val Tyr Tyr Cys
                85                  90                  95

Ala Arg Gly Gly Ile Phe Tyr Gly Met Asp Tyr Trp Gly Gln Gly Thr
            100                 105                 110

Leu Val Thr Val Ser Ser
        115

<210> SEQ ID NO 3
<211> LENGTH: 118
<212> TYPE: PRT
<213> ORGANISM: Artificial Sequence
<220> FEATURE:
<223> OTHER INFORMATION: Synthetic Construct

<400> SEQUENCE: 3

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asp Tyr
            20                  25                  30

Asp Ile His Trp Val Arg Gln Ala Pro Gly Gln Gly Leu Glu Trp Ile
        35                  40                  45

Val Trp Ile Asn Thr Glu Thr Gly Glu Pro Thr Tyr Ala Asp Asp Phe
    50                  55                  60

Lys Gly Arg Val Thr Ile Thr Arg Asp Thr Ser Thr Ser Thr Ala Tyr
65                  70                  75                  80

Leu Glu Leu Ser Ser Leu Arg Ser Glu Asp Thr Ala Val Tyr Tyr Cys
                85                  90                  95

Ala Arg Glu Ile Leu Phe Tyr Gly Met Asp Tyr Trp Gly Gln Gly Thr
            100                 105                 110

Leu Val Thr Val Ser Ser
        115

<210> SEQ ID NO 4
<211> LENGTH: 119
<212> TYPE: PRT
<213> ORGANISM: Artificial Sequence
<220> FEATURE:
<223> OTHER INFORMATION: Synthetic Construct

<400> SEQUENCE: 4

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asp Tyr
            20                  25                  30

Phe Ile His Trp Val Arg Gln Ala Pro Gly Gln Gly Leu Glu Trp Ile
        35                  40                  45
```

```
Ala Gly Ile Val Tyr Asp Ala Thr Gly Phe Thr Thr Tyr Ala Asp Asp
     50                  55                  60
Phe Lys Gly Arg Val Thr Ile Thr Arg Asp Thr Ser Thr Ser Thr Ala
 65                  70                  75                  80
Tyr Leu Glu Leu Ser Ser Leu Arg Ser Glu Asp Thr Ala Val Tyr Tyr
                 85                  90                  95
Cys Ala Arg Gly Gly Ile Phe Tyr Gly Met Asp Tyr Trp Gly Gln Gly
                100                 105                 110
Thr Leu Val Thr Val Ser Ser
            115
```

<210> SEQ ID NO 5
<211> LENGTH: 108
<212> TYPE: PRT
<213> ORGANISM: Artificial Sequence
<220> FEATURE:
<223> OTHER INFORMATION: Synthetic Construct

<400> SEQUENCE: 5

```
Asp Ile Gln Met Thr Gln Ser Pro Ser Ser Leu Ser Ala Ser Val Gly
 1               5                  10                  15
Asp Arg Val Thr Ile Thr Cys Lys Ala Ser Gln Ser Val Ile Asn Asp
             20                  25                  30
Ala Ala Trp Tyr Gln Gln Lys Pro Gly Lys Ala Pro Lys Leu Leu Ile
         35                  40                  45
Tyr Tyr Thr Ser His Arg Tyr Thr Gly Val Pro Ser Arg Phe Ser Gly
     50                  55                  60
Ser Gly Ser Gly Thr Asp Phe Thr Leu Thr Ile Ser Ser Leu Gln Glu
 65                  70                  75                  80
Asp Phe Ala Thr Tyr Tyr Cys Gln Gln Asp Tyr Thr Pro Phe Pro Leu
                 85                  90                  95
Thr Phe Gly Gln Gly Thr Lys Val Glu Ile Lys Arg
                100                 105
```

<210> SEQ ID NO 6
<211> LENGTH: 118
<212> TYPE: PRT
<213> ORGANISM: Artificial Sequence
<220> FEATURE:
<223> OTHER INFORMATION: Synthetic Construct

<400> SEQUENCE: 6

```
Glu Val Gln Leu Val Gln Ser Gly Ala Glu Val Lys Lys Pro Gly Ala
 1               5                  10                  15
Ser Val Lys Val Ser Cys Lys Ala Ser Gly Tyr Thr Phe Thr Asp Tyr
             20                  25                  30
Leu Met His Trp Val Arg Gln Ala Pro Gly Gln Gly Leu Glu Trp Ile
         35                  40                  45
Ala Val Ile Val Ser Ile Thr Gly Arg Thr Tyr Tyr Ala Asp Asp Phe
     50                  55                  60
Lys Gly Arg Val Thr Ile Thr Arg Asp Thr Ser Thr Ser Thr Ala Tyr
 65                  70                  75                  80
Leu Glu Leu Ser Ser Leu Arg Ser Glu Asp Thr Ala Val Tyr Tyr Cys
                 85                  90                  95
Ala Arg Gly Gly Ile Phe Tyr Gly Met Asp Tyr Trp Gly Gln Gly Thr
                100                 105                 110
Leu Val Thr Val Ser Ser
            115
```

```
<210> SEQ ID NO 7
<211> LENGTH: 117
<212> TYPE: PRT
<213> ORGANISM: Artificial Sequence
<220> FEATURE:
<223> OTHER INFORMATION: Synthetic Construct

<400> SEQUENCE: 7
```

| Glu | Val | Gln | Leu | Val | Gln | Ser | Gly | Ala | Glu | Val | Lys | Lys | Pro | Gly | Ala |
|---|---|---|---|---|---|---|---|---|---|---|---|---|---|---|---|
| 1 | | | | 5 | | | | | 10 | | | | | 15 | |

| Ser | Val | Lys | Val | Ser | Cys | Lys | Ala | Ser | Gly | Tyr | Thr | Phe | Thr | Asp | Tyr |
|---|---|---|---|---|---|---|---|---|---|---|---|---|---|---|---|
| | | | 20 | | | | | 25 | | | | | 30 | | |

| Ser | Met | His | Trp | Val | Arg | Gln | Ala | Pro | Gly | Gln | Gly | Leu | Glu | Trp | Ile |
|---|---|---|---|---|---|---|---|---|---|---|---|---|---|---|---|
| | | 35 | | | | | 40 | | | | | 45 | | | |

| Gly | Val | Ile | Phe | Gln | Ser | Gly | Ala | Thr | Tyr | Tyr | Ala | Asp | Asp | Phe | Lys |
|---|---|---|---|---|---|---|---|---|---|---|---|---|---|---|---|
| | 50 | | | | | 55 | | | | | 60 | | | | |

| Gly | Arg | Val | Thr | Ile | Thr | Arg | Asp | Thr | Ser | Thr | Ser | Thr | Ala | Tyr | Leu |
|---|---|---|---|---|---|---|---|---|---|---|---|---|---|---|---|
| 65 | | | | | 70 | | | | | 75 | | | | | 80 |

| Glu | Leu | Ser | Ser | Leu | Arg | Ser | Glu | Asp | Thr | Ala | Val | Tyr | Tyr | Cys | Ala |
|---|---|---|---|---|---|---|---|---|---|---|---|---|---|---|---|
| | | | | 85 | | | | | 90 | | | | | 95 | |

| Arg | Gly | Gly | Ile | Phe | Tyr | Gly | Met | Asp | Tyr | Trp | Gly | Gln | Gly | Thr | Leu |
|---|---|---|---|---|---|---|---|---|---|---|---|---|---|---|---|
| | | | 100 | | | | | 105 | | | | | 110 | | |

| Val | Thr | Val | Ser | Ser |
|---|---|---|---|---|
| | | | | 115 |

```
<210> SEQ ID NO 8
<211> LENGTH: 117
<212> TYPE: PRT
<213> ORGANISM: Artificial Sequence
<220> FEATURE:
<223> OTHER INFORMATION: Synthetic Construct

<400> SEQUENCE: 8
```

| Glu | Val | Gln | Leu | Val | Gln | Ser | Gly | Ala | Glu | Val | Lys | Lys | Pro | Gly | Ala |
|---|---|---|---|---|---|---|---|---|---|---|---|---|---|---|---|
| 1 | | | | 5 | | | | | 10 | | | | | 15 | |

| Ser | Val | Lys | Val | Ser | Cys | Lys | Ala | Ser | Gly | Tyr | Thr | Phe | Thr | Asp | Tyr |
|---|---|---|---|---|---|---|---|---|---|---|---|---|---|---|---|
| | | | 20 | | | | | 25 | | | | | 30 | | |

| Ser | Met | His | Trp | Val | Arg | Gln | Ala | Pro | Gly | Gln | Gly | Leu | Glu | Trp | Ile |
|---|---|---|---|---|---|---|---|---|---|---|---|---|---|---|---|
| | | 35 | | | | | 40 | | | | | 45 | | | |

| Gly | Ile | Ile | Phe | Tyr | Thr | Gly | His | Thr | Tyr | Tyr | Ala | Asp | Asp | Phe | Lys |
|---|---|---|---|---|---|---|---|---|---|---|---|---|---|---|---|
| | 50 | | | | | 55 | | | | | 60 | | | | |

| Gly | Arg | Val | Thr | Ile | Thr | Arg | Asp | Thr | Ser | Thr | Ser | Thr | Ala | Tyr | Leu |
|---|---|---|---|---|---|---|---|---|---|---|---|---|---|---|---|
| 65 | | | | | 70 | | | | | 75 | | | | | 80 |

| Glu | Leu | Ser | Ser | Leu | Arg | Ser | Glu | Asp | Thr | Ala | Val | Tyr | Tyr | Cys | Ala |
|---|---|---|---|---|---|---|---|---|---|---|---|---|---|---|---|
| | | | | 85 | | | | | 90 | | | | | 95 | |

| Arg | Gly | Gly | Ile | Phe | Tyr | Gly | Met | Asp | Tyr | Trp | Gly | Gln | Gly | Thr | Leu |
|---|---|---|---|---|---|---|---|---|---|---|---|---|---|---|---|
| | | | 100 | | | | | 105 | | | | | 110 | | |

| Val | Thr | Val | Ser | Ser |
|---|---|---|---|---|
| | | | | 115 |

```
<210> SEQ ID NO 9
<211> LENGTH: 11
<212> TYPE: PRT
<213> ORGANISM: Artificial Sequence
<220> FEATURE:
<223> OTHER INFORMATION: Synthetic Construct

<400> SEQUENCE: 9
```

Lys Ala Ser Gln Ser Val Ile Asn Asp Ala Ala
1               5                   10

<210> SEQ ID NO 10
<211> LENGTH: 7
<212> TYPE: PRT
<213> ORGANISM: Artificial Sequence
<220> FEATURE:
<223> OTHER INFORMATION: Synthetic Construct

<400> SEQUENCE: 10

Tyr Thr Ser His Arg Tyr Thr
1               5

<210> SEQ ID NO 11
<211> LENGTH: 10
<212> TYPE: PRT
<213> ORGANISM: Artificial Sequence
<220> FEATURE:
<223> OTHER INFORMATION: Synthetic Construct

<400> SEQUENCE: 11

Gln Gln Asp Tyr Thr Ser Pro Trp Thr Phe
1               5                   10

<210> SEQ ID NO 12
<211> LENGTH: 11
<212> TYPE: PRT
<213> ORGANISM: Artificial Sequence
<220> FEATURE:
<223> OTHER INFORMATION: Synthetic Construct

<400> SEQUENCE: 12

Gln Gln Asp Tyr Thr Pro Phe Pro Leu Thr Phe
1               5                   10

<210> SEQ ID NO 13
<211> LENGTH: 5
<212> TYPE: PRT
<213> ORGANISM: Artificial Sequence
<220> FEATURE:
<223> OTHER INFORMATION: Synthetic Construct

<400> SEQUENCE: 13

Asp Tyr Ser Met His
1               5

<210> SEQ ID NO 14
<211> LENGTH: 5
<212> TYPE: PRT
<213> ORGANISM: Artificial Sequence
<220> FEATURE:
<223> OTHER INFORMATION: Synthetic Construct

<400> SEQUENCE: 14

Asp Tyr Asp Ile His
1               5

<210> SEQ ID NO 15
<211> LENGTH: 5
<212> TYPE: PRT
<213> ORGANISM: Artificial Sequence
<220> FEATURE:
<223> OTHER INFORMATION: Synthetic Construct

<400> SEQUENCE: 15

Asp Tyr Phe Ile His

```
1               5

<210> SEQ ID NO 16
<211> LENGTH: 5
<212> TYPE: PRT
<213> ORGANISM: Artificial Sequence
<220> FEATURE:
<223> OTHER INFORMATION: Synthetic Construct

<400> SEQUENCE: 16

Asp Tyr Leu Met His
1               5

<210> SEQ ID NO 17
<211> LENGTH: 17
<212> TYPE: PRT
<213> ORGANISM: Artificial Sequence
<220> FEATURE:
<223> OTHER INFORMATION: Synthetic Construct

<400> SEQUENCE: 17

Val Trp Ile Asn Thr Glu Thr Gly Glu Pro Thr Tyr Ala Asp Asp Phe
1               5                   10                  15

Lys

<210> SEQ ID NO 18
<211> LENGTH: 18
<212> TYPE: PRT
<213> ORGANISM: Artificial Sequence
<220> FEATURE:
<223> OTHER INFORMATION: Synthetic Construct

<400> SEQUENCE: 18

Ala Gly Ile Val Tyr Asp Ala Thr Gly Phe Thr Thr Tyr Ala Asp Asp
1               5                   10                  15

Phe Lys

<210> SEQ ID NO 19
<211> LENGTH: 17
<212> TYPE: PRT
<213> ORGANISM: Artificial Sequence
<220> FEATURE:
<223> OTHER INFORMATION: Synthetic Construct

<400> SEQUENCE: 19

Ala Val Ile Val Ser Ile Thr Gly Arg Thr Tyr Tyr Ala Asp Asp Phe
1               5                   10                  15

Lys

<210> SEQ ID NO 20
<211> LENGTH: 9
<212> TYPE: PRT
<213> ORGANISM: Artificial Sequence
<220> FEATURE:
<223> OTHER INFORMATION: Synthetic Construct

<400> SEQUENCE: 20

Gly Gly Ile Phe Tyr Gly Met Asp Tyr
1               5

<210> SEQ ID NO 21
<211> LENGTH: 9
<212> TYPE: PRT
<213> ORGANISM: Artificial Sequence
<220> FEATURE:
```

<223> OTHER INFORMATION: Synthetic Construct

<400> SEQUENCE: 21

Glu Ile Leu Phe Tyr Gly Met Asp Tyr
1               5

<210> SEQ ID NO 22
<211> LENGTH: 16
<212> TYPE: PRT
<213> ORGANISM: Artificial Sequence
<220> FEATURE:
<223> OTHER INFORMATION: Synthetic Construct

<400> SEQUENCE: 22

Gly Val Ile Phe Gln Ser Gly Ala Thr Tyr Tyr Ala Asp Asp Phe Lys
1               5                   10                  15

<210> SEQ ID NO 23
<211> LENGTH: 16
<212> TYPE: PRT
<213> ORGANISM: Artificial Sequence
<220> FEATURE:
<223> OTHER INFORMATION: Synthetic Construct

<400> SEQUENCE: 23

Gly Ile Ile Phe Tyr Thr Gly His Thr Tyr Tyr Ala Asp Asp Phe Lys
1               5                   10                  15

<210> SEQ ID NO 24
<211> LENGTH: 10
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (5)..(5)
<223> OTHER INFORMATION: Xaa is Thr, Ile, Lys, or Leu
<220> FEATURE:
<221> NAME/KEY: MISC_FEATURE
<222> LOCATION: (6)..(6)
<223> OTHER INFORMATION: Xaa is Ser or His

<400> SEQUENCE: 24

Gln Gln Asp Tyr Xaa Xaa Pro Trp Thr Phe
1               5                   10

<210> SEQ ID NO 25
<211> LENGTH: 18
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (1)..(1)
<223> OTHER INFORMATION: Xaa is Ala or Gly
<220> FEATURE:
<221> NAME/KEY: MISC_FEATURE
<222> LOCATION: (12)..(12)
<223> OTHER INFORMATION: Xaa is Thr, Ile, Val, or Ala
<220> FEATURE:
<221> NAME/KEY: MISC_FEATURE
<222> LOCATION: (15)..(15)
<223> OTHER INFORMATION: Xaa is Asp, Val, or Glu
<220> FEATURE:
<221> NAME/KEY: MISC_FEATURE
<222> LOCATION: (16)..(16)
<223> OTHER INFORMATION: Xaa is Asp, Glu, Asn, Ser, Ile, Leu, Thr, Ala,
      or Phe

```
<400> SEQUENCE: 25

Xaa Gly Ile Val Tyr Asp Ala Thr Gly Phe Thr Xaa Tyr Ala Xaa Xaa
1               5                   10                  15

Phe Lys

<210> SEQ ID NO 26
<211> LENGTH: 14
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (3)..(3)
<223> OTHER INFORMATION: Xaa is Val or Phe
<220> FEATURE:
<221> NAME/KEY: MISC_FEATURE
<222> LOCATION: (7)..(7)
<223> OTHER INFORMATION: Xaa is Arg or Ile
<220> FEATURE:
<221> NAME/KEY: MISC_FEATURE
<222> LOCATION: (9)..(9)
<223> OTHER INFORMATION: Xaa is Thr, Phe, Met, or Pro
<220> FEATURE:
<221> NAME/KEY: MISC_FEATURE
<222> LOCATION: (14)..(14)
<223> OTHER INFORMATION: Xaa is Ala or Val.

<400> SEQUENCE: 26

Gly Arg Xaa Thr Ile Thr Xaa Asp Xaa Ser Thr Ser Thr Xaa
1               5                   10

<210> SEQ ID NO 27
<211> LENGTH: 10
<212> TYPE: PRT
<213> ORGANISM: Artificial Sequence
<220> FEATURE:
<223> OTHER INFORMATION: Synthetic Construct

<400> SEQUENCE: 27

Gln Gln Asp Tyr Thr His Pro Trp Thr Phe
1               5                   10

<210> SEQ ID NO 28
<211> LENGTH: 18
<212> TYPE: PRT
<213> ORGANISM: Artificial Sequence
<220> FEATURE:
<223> OTHER INFORMATION: Synthetic Construct

<400> SEQUENCE: 28

Gly Gly Ile Val Tyr Asp Ala Thr Gly Phe Thr Thr Tyr Ala Glu Glu
1               5                   10                  15

Phe Lys

<210> SEQ ID NO 29
<211> LENGTH: 107
<212> TYPE: PRT
<213> ORGANISM: Artificial Sequence
<220> FEATURE:
<223> OTHER INFORMATION: Synthetic Construct

<400> SEQUENCE: 29

Asp Ile Gln Met Thr Gln Ser Pro Ser Ser Leu Ser Ala Ser Val Gly
1               5                   10                  15

Asp Arg Val Thr Ile Thr Cys Lys Ala Ser Gln Ser Val Ile Asn Asp
                20                  25                  30
```

Ala Ala Trp Tyr Gln Gln Lys Pro Gly Lys Ala Pro Lys Leu Leu Ile
            35                  40                  45

Tyr Tyr Thr Ser His Arg Tyr Thr Gly Val Pro Ser Arg Phe Ser Gly
        50                  55                  60

Ser Gly Ser Gly Thr Asp Phe Thr Leu Thr Ile Ser Ser Leu Gln Glu
65                  70                  75                  80

Asp Phe Ala Thr Tyr Tyr Cys Gln Gln Asp Tyr Thr His Pro Trp Thr
                85                  90                  95

Phe Gly Gln Gly Thr Lys Val Glu Ile Lys Arg
            100                 105

<210> SEQ ID NO 30
<211> LENGTH: 119
<212> TYPE: PRT
<213> ORGANISM: Artificial Sequence
<220> FEATURE:
<223> OTHER INFORMATION: Synthetic Construct

<400> SEQUENCE: 30

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asp Tyr
                20                  25                  30

Phe Ile His Trp Val Arg Gln Ala Pro Gly Gln Gly Leu Glu Trp Ile
            35                  40                  45

Gly Gly Ile Val Tyr Asp Ala Thr Gly Phe Thr Thr Tyr Ala Glu Glu
        50                  55                  60

Phe Lys Gly Arg Val Thr Ile Thr Arg Asp Thr Ser Thr Ser Thr Ala
65                  70                  75                  80

Tyr Leu Glu Leu Ser Ser Leu Arg Ser Glu Asp Thr Ala Val Tyr Tyr
                85                  90                  95

Cys Ala Arg Gly Gly Ile Phe Tyr Gly Met Asp Tyr Trp Gly Gln Gly
            100                 105                 110

Thr Leu Val Thr Val Ser Ser
        115

<210> SEQ ID NO 31
<211> LENGTH: 10
<212> TYPE: PRT
<213> ORGANISM: Artificial Sequence
<220> FEATURE:
<223> OTHER INFORMATION: Synthetic Construct

<400> SEQUENCE: 31

Gln Gln Asp Tyr Lys His Pro Trp Thr Phe
1               5                   10

<210> SEQ ID NO 32
<211> LENGTH: 18
<212> TYPE: PRT
<213> ORGANISM: Artificial Sequence
<220> FEATURE:
<223> OTHER INFORMATION: Synthetic Construct

<400> SEQUENCE: 32

Ala Gly Ile Val Tyr Asp Ala Thr Gly Phe Thr Val Tyr Ala Asp Asp
1               5                   10                  15

Phe Lys

```
<210> SEQ ID NO 33
<211> LENGTH: 107
<212> TYPE: PRT
<213> ORGANISM: Artificial Sequence
<220> FEATURE:
<223> OTHER INFORMATION: Synthetic Construct

<400> SEQUENCE: 33

Asp Ile Gln Met Thr Gln Ser Pro Ser Ser Leu Ser Ala Ser Val Gly
1               5                   10                  15

Asp Arg Val Thr Ile Thr Cys Lys Ala Ser Gln Ser Val Ile Asn Asp
                20                  25                  30

Ala Ala Trp Tyr Gln Gln Lys Pro Gly Lys Ala Pro Lys Leu Leu Ile
            35                  40                  45

Tyr Tyr Thr Ser His Arg Tyr Thr Gly Val Pro Ser Arg Phe Ser Gly
    50                  55                  60

Ser Gly Ser Gly Thr Asp Phe Thr Leu Thr Ile Ser Ser Leu Gln Glu
65                  70                  75                  80

Asp Phe Ala Thr Tyr Tyr Cys Gln Gln Asp Tyr Lys His Pro Trp Thr
                85                  90                  95

Phe Gly Gln Gly Thr Lys Val Glu Ile Lys Arg
            100                 105

<210> SEQ ID NO 34
<211> LENGTH: 119
<212> TYPE: PRT
<213> ORGANISM: Artificial Sequence
<220> FEATURE:
<223> OTHER INFORMATION: Synthetic Construct

<400> SEQUENCE: 34

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asp Tyr
                20                  25                  30

Phe Ile His Trp Val Arg Gln Ala Pro Gly Gln Gly Leu Glu Trp Ile
            35                  40                  45

Ala Gly Ile Val Tyr Asp Ala Thr Gly Phe Thr Val Tyr Ala Asp Asp
    50                  55                  60

Phe Lys Gly Arg Val Thr Ile Thr Arg Asp Thr Ser Thr Ser Thr Ala
65                  70                  75                  80

Tyr Leu Glu Leu Ser Ser Leu Arg Ser Glu Asp Thr Ala Val Tyr Tyr
                85                  90                  95

Cys Ala Arg Gly Gly Ile Phe Tyr Gly Met Asp Tyr Trp Gly Gln Gly
            100                 105                 110

Thr Leu Val Thr Val Ser Ser
        115
```